United States Patent
Wagner et al.

(10) Patent No.: US 8,784,496 B2
(45) Date of Patent: *Jul. 22, 2014

(54) ORTHOPAEDIC KNEE PROSTHESIS HAVING CONTROLLED CONDYLAR CURVATURE

(75) Inventors: Christel M. Wagner, Plymouth, IN (US); Dimitri Sokolov, Copley, OH (US); Jordan S. Lee, Warsaw, IN (US); John L. Williams, Fort Wayne, IN (US); Said T. Gomaa, Fort Wayne, IN (US); John M. Armacost, Warsaw, IN (US)

(73) Assignee: DePuy (Ireland) (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,990

(22) Filed: Jun. 4, 2012

(65) Prior Publication Data

US 2012/0239158 A1     Sep. 20, 2012

Related U.S. Application Data

(63) Continuation of application No. 12/165,574, filed on Jun. 30, 2008, now Pat. No. 8,192,498.

(51) Int. Cl.
*A61F 2/38* (2006.01)

(52) U.S. Cl.
USPC ..................... 623/20.21; 623/20.31

(58) Field of Classification Search
USPC ............................. 623/20.14–20.31
See application file for complete search history.

(56) References Cited

U.S. PATENT DOCUMENTS

| | | |
|---|---|---|
| 3,765,033 A | 10/1973 | Goldberg et al. |
| 3,840,905 A | 10/1974 | Deane |
| 3,852,045 A | 12/1974 | Wheeler et al. |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |
| 4,209,861 A | 7/1980 | Walker et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |

(Continued)

FOREIGN PATENT DOCUMENTS

| | | |
|---|---|---|
| CN | 1803106 A | 7/2006 |
| CN | 1872009 A | 12/2006 |

(Continued)

OTHER PUBLICATIONS

European Search Report for European Patent Application No. 09164235.5-1526, Dec. 22, 2009, 6 pgs.

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopaedic knee prosthesis includes a tibial bearing and a femoral component configured to articulate with the tibial bearing. The femoral component includes a condyle surface curved in the sagittal plane. The radius of curvature of the condyle surface decreases gradually between early-flexion and mid-flexion. Additionally, in some embodiments, the radius of curvature may be increased during mid-flexion.

19 Claims, 13 Drawing Sheets

(56) References Cited

U.S. PATENT DOCUMENTS

| | | |
|---|---|---|
| 4,612,160 A | 9/1986 | Donlevy et al. |
| 4,673,407 A | 6/1987 | Martin |
| 4,714,474 A | 12/1987 | Brooks, Jr. et al. |
| 4,795,468 A | 1/1989 | Hodorek et al. |
| 4,808,185 A | 2/1989 | Penenberg et al. |
| 4,822,362 A | 4/1989 | Walker et al. |
| 4,838,891 A | 6/1989 | Branemark et al. |
| 4,888,021 A | 12/1989 | Forte et al. |
| 4,938,769 A | 7/1990 | Shaw |
| 4,944,757 A | 7/1990 | Martinez et al. |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne et al. |
| 5,007,933 A | 4/1991 | Sidebotham et al. |
| 5,011,496 A | 4/1991 | Forte et al. |
| 5,019,103 A | 5/1991 | Van Zile et al. |
| 5,037,423 A | 8/1991 | Kenna |
| 5,071,438 A | 12/1991 | Jones et al. |
| 5,080,675 A | 1/1992 | Lawes et al. |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas et al. |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin et al. |
| 5,258,044 A | 11/1993 | Lee |
| 5,271,737 A | 12/1993 | Baldwin et al. |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker |
| 5,330,534 A | 7/1994 | Herrington et al. |
| 5,344,460 A | 9/1994 | Turanyi et al. |
| 5,344,461 A | 9/1994 | Philpot |
| 5,344,494 A | 9/1994 | Davidson et al. |
| 5,358,527 A | 10/1994 | Forte |
| 5,368,881 A | 11/1994 | Kelman et al. |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun et al. |
| 5,449,745 A | 9/1995 | Sun et al. |
| 5,458,637 A | 10/1995 | Hayes |
| 5,480,446 A | 1/1996 | Goodfellow et al. |
| 5,543,471 A | 8/1996 | Sun et al. |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun et al. |
| 5,658,333 A | 8/1997 | Kelman et al. |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier et al. |
| 5,702,464 A | 12/1997 | Lackey et al. |
| 5,702,466 A | 12/1997 | Pappas et al. |
| 5,728,748 A | 3/1998 | Sun et al. |
| 5,732,469 A | 3/1998 | Hamamoto et al. |
| 5,755,800 A | 5/1998 | O'Neil et al. |
| 5,755,801 A | 5/1998 | Walker et al. |
| 5,755,803 A | 5/1998 | Haines et al. |
| 5,765,095 A | 6/1998 | Flak et al. |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hoffmann |
| 5,871,545 A | 2/1999 | Goodfellow et al. |
| 5,871,546 A | 2/1999 | Colleran et al. |
| 5,879,394 A | 3/1999 | Ashby et al. |
| 5,879,400 A | 3/1999 | Merrill et al. |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman et al. |
| 5,964,808 A | 10/1999 | Blaha et al. |
| 5,976,147 A | 11/1999 | LaSalle et al. |
| 5,984,969 A | 11/1999 | Matthews et al. |
| 5,989,027 A | 11/1999 | Wagner et al. |
| 5,997,577 A | 12/1999 | Herrington et al. |
| 6,004,351 A | 12/1999 | Tomita et al. |
| 6,005,018 A | 12/1999 | Cicierega et al. |
| 6,010,534 A | 1/2000 | O'Neil et al. |
| 6,013,103 A | 1/2000 | Kaufman et al. |
| 6,017,975 A | 1/2000 | Saum et al. |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal-Or et al. |
| 6,068,658 A | 5/2000 | Insall et al. |
| 6,080,195 A | 6/2000 | Colleran et al. |
| 6,090,144 A | 7/2000 | Letot et al. |
| 6,123,728 A | 9/2000 | Brosnahan et al. |
| 6,123,729 A | 9/2000 | Insall et al. |
| 6,123,896 A | 9/2000 | Meeks, III et al. |
| 6,126,692 A | 10/2000 | Robie et al. |
| 6,135,857 A | 10/2000 | Shaw et al. |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun et al. |
| 6,206,926 B1 | 3/2001 | Pappas |
| 6,210,444 B1 | 4/2001 | Webster et al. |
| 6,210,445 B1 | 4/2001 | Zawadzki |
| 6,217,618 B1 | 4/2001 | Hileman |
| 6,228,900 B1 | 5/2001 | Shen et al. |
| 6,238,434 B1 | 5/2001 | Pappas |
| 6,242,507 B1 | 6/2001 | Saum et al. |
| 6,245,276 B1 | 6/2001 | McNulty et al. |
| 6,258,127 B1 | 7/2001 | Schmotzer |
| 6,264,697 B1 | 7/2001 | Walker |
| 6,280,476 B1 | 8/2001 | Metzger et al. |
| 6,281,264 B1 | 8/2001 | Salovey et al. |
| 6,299,646 B1 | 10/2001 | Chambat et al. |
| 6,316,158 B1 | 11/2001 | Saum et al. |
| 6,319,283 B1 | 11/2001 | Insall et al. |
| 6,325,828 B1 | 12/2001 | Dennis et al. |
| 6,344,059 B1 | 2/2002 | Krakovits et al. |
| 6,361,564 B1 | 3/2002 | Marceaux et al. |
| 6,372,814 B1 | 4/2002 | Sun et al. |
| 6,379,388 B1 | 4/2002 | Ensign et al. |
| 6,428,577 B1 | 8/2002 | Evans et al. |
| 6,443,991 B1 | 9/2002 | Running |
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot et al. |
| 6,506,216 B1 | 1/2003 | McCue et al. |
| 6,524,522 B2 | 2/2003 | Vaidyanathan et al. |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee et al. |
| 6,589,283 B1 | 7/2003 | Metzger et al. |

(56) References Cited

U.S. PATENT DOCUMENTS

| | | |
|---|---|---|
| 6,592,787 B2 | 7/2003 | Pickrell et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre et al. |
| 6,664,308 B2 | 12/2003 | Sun et al. |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun et al. |
| 6,846,327 B2 | 1/2005 | Khandkar et al. |
| 6,846,329 B2 | 1/2005 | McMinn |
| 6,849,230 B1 | 2/2005 | Feichtinger |
| 6,852,272 B2 | 2/2005 | Artz et al. |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey et al. |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown et al. |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram et al. |
| 7,160,330 B2 | 1/2007 | Axelson, Jr. et al. |
| 7,175,665 B2 | 2/2007 | German et al. |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burstein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kucynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton et al. |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,192,498 B2 | 6/2012 | Wagner et al. |
| 8,206,451 B2 | 6/2012 | Wyss et al. |
| 8,236,061 B2 | 8/2012 | Heldreth et al. |
| 2002/0138150 A1 | 9/2002 | Leclercq |
| 2003/0009232 A1 | 1/2003 | Metzger et al. |
| 2003/0035747 A1 | 2/2003 | Anderson et al. |
| 2003/0044301 A1 | 3/2003 | Lefebvre et al. |
| 2003/0075013 A1 | 4/2003 | Grohowski |
| 2003/0139817 A1 | 7/2003 | Tuke et al. |
| 2003/0153981 A1 | 8/2003 | Wang et al. |
| 2003/0171820 A1 | 9/2003 | Wilshaw et al. |
| 2003/0199985 A1 | 10/2003 | Masini |
| 2003/0212161 A1 | 11/2003 | McKellop et al. |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen et al. |
| 2004/0186583 A1 | 9/2004 | Keller |
| 2004/0215345 A1 | 10/2004 | Perrone, Jr. et al. |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier et al. |
| 2005/0059750 A1 | 3/2005 | Sun et al. |
| 2005/0069629 A1 | 3/2005 | Becker et al. |
| 2005/0096747 A1 | 5/2005 | Tuttle et al. |
| 2005/0100578 A1 | 5/2005 | Schmid et al. |
| 2005/0123672 A1 | 6/2005 | Justin et al. |
| 2005/0143832 A1 | 6/2005 | Carson |
| 2005/0154472 A1 | 7/2005 | Afriat |
| 2005/0203631 A1 | 9/2005 | Daniels et al. |
| 2005/0209701 A1 | 9/2005 | Suguro et al. |
| 2005/0209702 A1 | 9/2005 | Todd et al. |
| 2005/0249625 A1 | 11/2005 | Bram et al. |
| 2005/0278035 A1 | 12/2005 | Wyss et al. |
| 2006/0002810 A1 | 1/2006 | Grohowski, Jr. |
| 2006/0015185 A1 | 1/2006 | Chambat et al. |
| 2006/0036329 A1 | 2/2006 | Webster et al. |
| 2006/0052875 A1 | 3/2006 | Bernero et al. |
| 2006/0100714 A1 | 5/2006 | Ensign |
| 2006/0178749 A1 | 8/2006 | Pendleton et al. |
| 2006/0195195 A1 | 8/2006 | Burstein et al. |
| 2006/0228247 A1 | 10/2006 | Grohowski |
| 2006/0231402 A1 | 10/2006 | Clasen et al. |
| 2006/0241781 A1 | 10/2006 | Brown et al. |
| 2006/0257358 A1 | 11/2006 | Wen et al. |
| 2006/0271191 A1 | 11/2006 | Hermansson |
| 2006/0289388 A1 | 12/2006 | Yang et al. |
| 2007/0061014 A1 | 3/2007 | Naegerl |
| 2007/0073409 A1 | 3/2007 | Cooney, III et al. |
| 2007/0078521 A1 | 4/2007 | Overholser et al. |
| 2007/0100463 A1 | 5/2007 | Aram et al. |
| 2007/0129809 A1 | 6/2007 | Meridew et al. |
| 2007/0135926 A1 | 6/2007 | Walker |
| 2007/0173948 A1 | 7/2007 | Meridew et al. |
| 2007/0196230 A1 | 8/2007 | Hamman et al. |
| 2007/0203582 A1 | 8/2007 | Campbell |
| 2007/0219639 A1 | 9/2007 | Otto et al. |
| 2007/0293647 A1 | 12/2007 | McKellop et al. |
| 2008/0004708 A1 | 1/2008 | Wyss |
| 2008/0021566 A1 | 1/2008 | Peters et al. |
| 2008/0091272 A1 | 4/2008 | Aram et al. |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Salvage et al. |
| 2008/0195108 A1 | 8/2008 | Bhatnagar et al. |
| 2008/0199720 A1 | 8/2008 | Liu |
| 2008/0206297 A1 | 8/2008 | Roeder et al. |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck et al. |
| 2009/0084491 A1 | 4/2009 | Uthgenannt et al. |
| 2009/0088859 A1 | 4/2009 | Hazebrouck et al. |
| 2009/0125114 A1 | 5/2009 | May et al. |
| 2009/0192610 A1 | 7/2009 | Case et al. |

(56) References Cited

U.S. PATENT DOCUMENTS

| | | |
|---|---|---|
| 2009/0265012 A1 | 10/2009 | Engh et al. |
| 2009/0265013 A1 | 10/2009 | Mandell |
| 2009/0292365 A1 | 11/2009 | Smith et al. |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0063594 A1 | 3/2010 | Hazebrouck et al. |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu et al. |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett et al. |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |
| 2011/0029090 A1 | 2/2011 | Zannis et al. |
| 2011/0029092 A1 | 2/2011 | Deruntz et al. |
| 2011/0035017 A1 | 2/2011 | Deffenbaugh et al. |
| 2011/0035018 A1 | 2/2011 | Deffenbaugh et al. |
| 2011/0106268 A1 | 5/2011 | Deffenbaugh et al. |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0259417 A1 | 10/2012 | Wyss et al. |
| 2013/0006372 A1 | 1/2013 | Wyss et al. |

FOREIGN PATENT DOCUMENTS

| | | |
|---|---|---|
| DE | 4308563 A1 | 9/1994 |
| DE | 19529824 A1 | 2/1997 |
| EP | 510178 | 5/1992 |
| EP | 0495340 A1 | 7/1992 |
| EP | 0634155 | 1/1995 |
| EP | 0636352 A2 | 2/1995 |
| EP | 0732091 A2 | 9/1996 |
| EP | 883388 | 12/1998 |
| EP | 0634156 B1 | 5/1999 |
| EP | 1129676 A1 | 5/2001 |
| EP | 0765645 B1 | 8/2003 |
| EP | 1374805 A2 | 2/2004 |
| EP | 1421918 A1 | 5/2004 |
| EP | 1440675 A1 | 7/2004 |
| EP | 1196118 | 10/2004 |
| EP | 1470801 | 10/2004 |
| EP | 0732092 B1 | 2/2005 |
| EP | 1591082 A2 | 2/2005 |
| EP | 1518521 A2 | 3/2005 |
| EP | 1226799 B1 | 5/2005 |
| EP | 1779812 A1 | 5/2007 |
| EP | 1923079 A1 | 5/2008 |
| FR | 2417971 A1 | 2/1979 |
| FR | 2621243 A1 | 4/1989 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 | 4/1967 |
| GB | 2293109 A | 3/1996 |
| GB | 2335145 A | 9/1999 |
| JP | 62205201 A | 9/1987 |
| JP | 8500992 T | 2/1996 |
| JP | 08224263 A1 | 9/1996 |
| JP | 2002291779 A1 | 10/2002 |
| JP | 2004167255 A | 6/2004 |
| JP | 2006015133 A | 1/2006 |
| WO | 7900739 | 10/1979 |
| WO | 8906947 | 8/1989 |
| WO | 9014806 | 12/1990 |
| WO | 9601725 | 1/1996 |
| WO | 9623458 | 8/1996 |
| WO | 9624311 | 8/1996 |
| WO | 9624312 | 8/1996 |
| WO | 9846171 | 10/1998 |
| WO | 9927872 | 6/1999 |
| WO | 9966864 | 12/1999 |
| WO | 0209624 A1 | 2/2002 |
| WO | 03039609 A1 | 5/2003 |
| WO | 03101647 A2 | 12/2003 |
| WO | 2004058108 A1 | 7/2004 |
| WO | 2004069104 A1 | 8/2004 |
| WO | 2005009489 A2 | 2/2005 |
| WO | 2005009729 A2 | 2/2005 |
| WO | 2005072657 A1 | 8/2005 |
| WO | 2005087125 A2 | 9/2005 |
| WO | 2006014294 A1 | 2/2006 |
| WO | 2006130350 A2 | 12/2006 |
| WO | 2007106172 A1 | 9/2007 |
| WO | 2007108804 A1 | 9/2007 |
| WO | 2007119173 A2 | 10/2007 |
| WO | 2008100784 A2 | 8/2008 |
| WO | 2009046212 A2 | 4/2009 |
| WO | 2009128943 A2 | 10/2009 |

OTHER PUBLICATIONS

European Search Report for European Patent Application No. 09164168.8-1526, Jan. 4, 2010, 6 pgs.

Vanguard Complete Knee System, Biomet, available at: http://www.biomet.com/patients/vanguard.sub.—complete.cfm, downloaded on Feb. 2009, (3 pages).

"NexGen Complete Knee Solution Cruciate Retaining Knee (CR)," Zimmer, available at: http://zimmer.com.au/ctl?template=PC&op=global&action=&template=PC&id=356- , downloaded on Feb. 18, 2009, (1 page).

Scorpio Knee TS Single Axis Revision Knee System, Stryker Orthopaedics, http://www.stryker.com/stellent/groups/public/documents/web.sub.—prod/02- 3609.pdf, (6 pages).

P. Johal et al, "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).

Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, (4 pages).

Asano et al. "In Vivo Three-Dimensional Knee Kinematics Using a Biplanar Image-Matching Technique," Clin Orthop Rel Res, 388: 157-166, 2001, (10 pages).

European Search Report for European Patent Application No. 09164160.5-1526, Jan. 4, 2010, 4 pgs.

European Search Report for European Patent Application No. 09164228.0-1526, Feb. 2, 2010, 6 pgs.

Kessler et al., "Sagittal curvature of total knee replacements predicts in vivo kinematics," Clinical Biomechanics 22(1): 52-58, 2007.

Wang et al., "Biomechanical differences exhibited during sit-to-stand between total knee arthroplasty designs of varying radii," J Arthroplasty 21(8): 1196-9, 2006.

Saari et al., "The effect of tibial insert design on rising from a chair; motion analysis after total knee replacement," Clin Biomech 19(9): 951-6, 2004.

(56) References Cited

OTHER PUBLICATIONS

Ranawat, "Design may be counterproductive for optimizing flexion after TKR," Clin Orthop Rel Res 416: 174-6, 2003.
D'Lima et al., "Quadriceps moment arm and quadriceps forces after total knee arthroplasty," Clin Orthop Rel Res 393:213-20, 2001.
Uvehammer et al., "In vivo kinematics of total knee arthroplasty: flat compared with concave tibial joint surface," J Orthop Res 18(6): 856-64, 2000.
Dennis et al., "In vivo anteroposterior femorotibial translation of total knee arthroplasty: a multicenter analysis," Clin Orthop Rel Res, 356: 47-57, 1998.
Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.
Wang et al., "A biomechanical comparison between the single-axis and multi-axis total knee arthroplasty systems for stand-to-sit movement," Clin Biomech 20(4): 428-33, 2005.
Dennis et al., "Multicenter Determination of in Vivo Kinematics After Total Knee Arthroplasty," Clin. Orthop. Rel. Res., 416, 37-57, 21 pgs.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
Suggs et al., "Three-Dimensional Tibiofemoral Articular Contact Kinematics of a Cruciate-Retaining Total Knee Arthroplasty," JBJS-Am, vol. 88, No. 2, 2006, 10 pgs.
Dennis et al., "In Vivo Determination of Normal and Anterior Cruciate Ligament-Deficient Knee Kinematics," J. Biomechanics, 38, 241-253, 2005, 13 pgs.
Li et al., "Anterior Cruciate Ligament Deficiency Alters the in Vivo Motion of the Tibiofemoral Cartilage Contact Points in Both Anteroposterior and Mediolateral Directions," JBJS-Am, vol. 88, No. 8, Aug. 2006, 10 pgs.
Ries, "Effect of ACL Sacrifice, Retention, or Substitution on K After TKA," http://www.orthosupersite.com/view.asp?rID=23134, Aug. 2007, 5 pgs.
Ferris, "Matching observed spiral form curves to equations of spirals in 2-D images," The First Japanese-Australian Joint Seminar, 7 pgs.
Goodfellow et al., "The Mechanics of the Knee and Prosthesis Design," The Journal of Bone and Joint Surgery, vol. 60-B, No. 3, 12 pgs.
Dennis, et al. "A Multi-Center Analysis of Axial Femorotibial Rotation After Total Knee Arthoplasty", Clinical Orthopaedics 428 (2004); 180-189, 10 Pages.
Fan, Cheng-Yu, et al., "Primitive Results After Medical-Pivot Knee Arthroplasties: A Minimum 5 Year Follow-Up Study", The Journal of Arthroplasty, vol. 25, No. 3 2010, 492-496, 5 Pages.
Freeman, M.A.R., et al., "The Movement of the Normal Tibio-Femoral Joint", The Journal of Biomechanics 38 (2005) (2), pp. 197-208, 12 Pgs.
Fuller, et al., "A Comparison of Lower-Extremity Skeletal Kinematics Measured Using Skin and Pin-Mounted Markers", Human Movement Science 16 (1997) 219-242, 24 Pages.
Komistek, et al., "In Vivo Flouroscopic Analysis of the Normal Human Knee", Clinical Orthopaedics 410 (2003): 69-81, 13 Pages.
Mannan, et al., "The Medial Rotation Total Knee Replacement: A Clinical and Radiological Review At a Mean Follow-Up of Six Years", The Journal of Bone and Joint Surgery, vol. 91-B, No. 6 (Jun. 2009): 750-756, 7 Pages.
Shaw et al., "The Longitudinal Axis of the Knee and the Role of the Cruciate Ligaments in Controlling Transverse Rotation", J.Bone Joint Surg. AM. 1974:56:1603-1609, 8 Pages.
Extended European Search Report, European Application No. 10174440.7-1526, Dec. 10, 2010, 4 Pages.

Extended European Search Report, European Application No. 10174439.9-1526, Dec. 20, 2010, 4 Pages.
European search report; European Application No. 10174439.9-1526; Dec. 20, 2010; 4 pages.
European Search Report for European Patent Application No. 09164245A-2310, Oct. 15, 2009, 5 pgs.
European Search Report for European Patent Application No. 11150648.1-2310, Apr. 7, 2011, 5 pgs.
Kurosawa, et al., "Geometry and Motion of the Knee for Implant and Orthotic Design", The Journal of Biomechanics 18 (1985), pp. 487-499, 12 pages.
Barnes, C.L., et al, "Kneeling is Safe for Patients Implanted With Medical-Pivot Total Knee Arthroplasty Designs, Journal of Arthoplasty", vol. 00, No. 0 2010, 1-6, 6 pages.
Blaha, et al., "Kinematics of the Human Knee Using an Open Chain Cadaver Model", Clinical Orthopaedics and Related Research, vol. 410 (2003); 25-34, 10 pages.
Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 Pages.
Karachalios, et al., "A Mid-Term Clinical Outcome Study of the Advance Medial Pivot Knee Arthroplasty", www.sciencedirect.come, The Knee 16 (2009); 484-488, 5 pages.
Komistek, et al., "In Vivo Polyethylene Bearing Mobility is Maintained in Posterior Stabilized Total Knee Arthroplasty", Clinical Orthopaedics 428 (2004): 207-213, 7 pages.
Koo, et al., "The Knee Joint Center of Rotation is Predominantly on the Lateral Side During Normal Walking", Journal of Biomechanics, vol. 41 (2008): 1269-1273, 5 pages.
Moonot, et al., "Correlation Between the Oxford Knee and American Knee Society Scores at Mid-Term Follow-Up", The Journal of Knee Surgery, vol. 22, No. 3 (Jul. 2009), 226-230, 5 Pages.
Murphy, Michael Charles, "Geometry and the Kinematics of the Normal Human Knee", Submitted to Masachusetts Institute of Technology (1990), 379 Pages.
Nakagawa, et al., "Tibiofemoral Movement 3: Full Flexion of the Normal Human Knee", J.Bone Joint Surg. AM, vol. 82-B, No. 8 (2000). 1199-1200, 2 Pages.
Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 pages.
Shakespeare, et al., "Flexion After Total Knee Replacement. A Comparison Between the Medical Pivot Knee and a Posterior Stabilised Knee", www.sciencedirect.com, The Knee 13 (2006): 371-372, 3 Pages.
Walker, et al., "Motion of a Mobile Bearing Knee Allowing Translation of Rotation", Journal of Arthroplasty 17 (2002): 11-19, 9 Pages.
European Patent Office, Search Report for App. No. 09164479.9-2310, mailed Nov. 4, 2009, 6 pages.
2ND Int'l Johnson-Elloy Knee Meeting, Mar. 1987, 9 pages.
Operative Technique, Johnson Elloy Knee System, Chas F. Thackray, Ltd., 1988, 34 pgs.
Operative Technique the Turning Point, Accord, the Johnson/Elloy Concept, Chas FL Thackray Ltd, 32 pages.
Restoration of Soft Tissue Stability, Johnson, et al., Chas. F. Thackray, Ltd., 21 pages.
The Turning Point, Accord, The Johnson Elloy Concept, Chas F. Thackray Ltd, 20 pages.
Prosthesis and Instrumentation The Turning Point, Accord, The Johnson/Elloy Concept, Chas F. Thackray Ltd, 8 pages.
Five to Eight Year Results of the Johnson/Elloy (Accord) Total Knee Arthroplasty, Johnson et al, The Journal of Arthroplasty, vol. 8, No. 1, Feb. 1993, 6 pages.
Factors Affecting the Range of Movement of Total Knee Arthroplasty, Harvey et al, The Journal of Bone and Joint Surgery, vol. 75-B, No. 6, Nov. 1993, 6 pages.
Advice Notice (NI) 2000/03, Defect & Investigation Centre, Mar. 13, 2000, 3 pages.
The Johnson Elloy (Accord) Total Knee Replacement, Norton et al, The Journal of Bone and Joint Surgery (BR), vol. 84, No. 6, Aug. 2002, 4 pages.

(56) References Cited

OTHER PUBLICATIONS

Midvatus Approach in Total Knee Arthroplasty, A Description and a Cadaveric Study Determining the Distance of the Popliteal Artery From the Patellar Margin of the Incision, Cooper et al., The Journal of Arthoplasty, vol. 14 No. 4, 1999, 4 pages.
European Search Report for European Patent Application No. 08164944.4- 2310-2042131, Mar. 16, 2009, 12 pgs.
Biomet, Vanguard Mono-Lock Tibial System, Patented Convertible Tibial Bearing Technology, 2009, 2 Pages.
Cari Zeiss, Zeiss Surfcomm 5000—"Contour and Surface Measuring Machines", 2005, 16 pages.
DePuy Inc., "AMK Total Knee System Product Brochure", 1996, 8 pages.
DePuy Knees International, "Sigma CR Porocoat.RTM.," 1 page.
DePuy Orthopaedics, Inc., "AMK Total Knee System Legent II Surgical Techinque", 1998, 30 pages.
DePuy Orthopaedics, Inc., "Sigma Fixed Bearing Knees—Function with Wear Resistance", 2010, 0612-65-508 (Rev. 1) 20 pages.
DePuy PFC Sigma RP, "PFC Sigma Knee System with Rotating Platform Technical Monograph", 1999, 0611-29-050 (Rev. 3), 70 pages.
Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages.
European Search Report for European Patent Application No. 08253140.1-2310, Dec. 23, 2008, 7 pgs.
European Search Report for European Patent Application No. 06739287.8-2310, Mar. 16, 2010, 3 Pages.
European Search Report for European Patent Application No. 09164478.1-2310, Oct. 20, 2009, 6 Pages.
European Search Report for European Patent Application No. 09164478.1-2310, Apr. 28, 2010, 12 Pages.
European Search Report for European Patent Application No. 10162138.1, Aug. 30, 2010, 7 Pages.
Japanese Search Report for Japanese Patent Application No. 2009-501393, Oct. 26, 2010, 5 Pages.
PCT Notification Concerning Transmittal of International Prel. Report for Corresponding International App. No. PCT/US2006/010431, Jun. 5, 2007, 89 Pages.
Procedure, References Guide for Use with P.F.C. Sigma Knee Systems, 1998, 8 pages.
The Effects of Conformity and Load in Total Knee Replacement, Kuster, et al, Clinical Orthopaedics and Related Research No. 375, Jun. 2000.
Zimmer Nexgen Trabecular Metal Tibial Tray, The Best Thing Next to Bone, 97-5954-001-00, 2007, 4 pages.
Zimmer, Trabecular Metal Monoblock Tibial Components, An Optimal Combination of Material and Design, www.zimmer.com, 2009, 3 pages.
European Seach Report for European Patent Application No. 09164235.5-1526, Dec. 22, 2009, 6 pgs.
Signus Medizintechnik, "PEEK-OPTIMA.RTM., The Polymer for Implants, Technical Information for the Medical Professional", 7 pages.
The Accuracy of Intramedullary Alignment in Total Knee Replacement, Elloy, et al, Chas F. Thackray Ltd, 12 pages.
PCT Notification concerning transmittal of International Preliminary Report for corresponding International Appl. No. PCT/US2006/010431, Dec. 2, 2008, 6 pages.

| Component Size | R1 | R2 | R3 | R4 | Ratio R1/R2 | Ratio R1/R3 | Ratio R1/R4 |
|---|---|---|---|---|---|---|---|
| 1 | 25.514 | 18.830 | 19.972 | 19.556 | 1.35 | 1.28 | 1.305 |
| 2 | 26.714 | 19.750 | 20.911 | 20.475 | 1.35 | 1.28 | 1.305 |
| 3 | 27.969 | 20.700 | 21.894 | 21.438 | 1.35 | 1.28 | 1.305 |
| 4 | 29.284 | 21.690 | 22.923 | 22.445 | 1.35 | 1.28 | 1.305 |
| 5 | 30.660 | 22.730 | 24.000 | 23.500 | 1.35 | 1.28 | 1.305 |
| 6 | 32.101 | 23.810 | 25.128 | 24.605 | 1.35 | 1.28 | 1.305 |
| 7 | 33.610 | 24.940 | 26.309 | 25.761 | 1.35 | 1.28 | 1.305 |
| 8 | 35.189 | 26.120 | 27.546 | 26.972 | 1.35 | 1.28 | 1.305 |
| 9 | 36.843 | 27.350 | 28.840 | 28.239 | 1.35 | 1.28 | 1.305 |
| 10 | 38.575 | 28.630 | 30.196 | 29.567 | 1.35 | 1.28 | 1.305 |

Fig. 10

| Component Size | Origin Distance | RAY LENGTH EQUATION |
|---|---|---|
| 1 | 4.008 | R=29.383391+0.016694187*θ−0.000270023780*θ²−0.00001248370*θ³ |
| 2 | 3.898 | R=30.470577+0.016694187*θ−0.000270023780*θ²−0.00001248370*θ³ |
| 3 | 3.722 | R=31.597988+0.016694187*θ−0.000270023780*θ²−0.00001248370*θ³ |
| 4 | 3.629 | R=32.767114+0.016694187*θ−0.000270023780*θ²−0.00001248370*θ³ |
| 5 | 3.468 | R=33.979497+0.016694187*θ−0.000270023780*θ²−0.00001248370*θ³ |
| 6 | 3.288 | R=35.236738+0.016694187*θ−0.000270023780*θ²−0.00001248370*θ³ |
| 7 | 3.088 | R=36.540498+0.016694187*θ−0.000270023780*θ²−0.00001248370*θ³ |
| 8 | 2.866 | R=37.892496+0.016694187*θ−0.000270023780*θ²−0.00001248370*θ³ |
| 9 | 2.623 | R=39.294518+0.016694187*θ−0.000270023780*θ²−0.00001248370*θ³ |
| 10 | 2.356 | R=40.748416+0.016694187*θ−0.000270023780*θ²−0.00001248370*θ³ |

Fig. 12

ORTHOPAEDIC KNEE PROSTHESIS HAVING CONTROLLED CONDYLAR CURVATURE

This patent application is a continuation of U.S. Utility patent application Ser. No. 12/165,574, now U.S. Pat. No. 8,192,498, entitled "POSTERIOR CRUCIATE-RETAINING ORTHOPAEDIC KNEE PROSTHESIS HAVING CONTROLLED CONDYLAR CURVATURE," by Christel M. Wagner, which was filed on Jun. 30, 2008, the entirety of which is expressly incorporated herein by reference.

CROSS-REFERENCE TO RELATED U.S. PATENT APPLICATION

Cross-reference is made to U.S. Utility patent application Ser. No. 12/165,575 entitled "Posterior Stabilized Orthopaedic Knee Prosthesis Having Controlled Condylar Curvature" by Joseph G. Wyss, which was filed on Jun. 30, 2008; to U.S. Utility patent application Ser. No. 12/165,579 entitled "Orthopaedic Femoral Component Having Controlled Condylar Curvature" by John L. Williams, which was filed on Jun. 30, 2008; to U.S. Utility patent application Ser. No. 12/165,582 entitled "Posterior Stabilized Orthopaedic Prosthesis" by Joseph G. Wyss, which was filed on Jun. 30, 2008; and to U.S. Utility patent application Ser. No. 12/488,107 entitled "Orthopaedic Knee Prosthesis Having Controlled Condylar Curvature" by Mark A. Heldreth, which was filed on Jun. 19, 2009; the entirety of each of which is incorporated herein by reference.

TECHNICAL FIELD

The present disclosure relates generally to orthopaedic prostheses, and particularly to orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial bearing in cases wherein it is desirable to limit the movement of the knee prosthesis, such as when significant soft tissue damage or loss is present. Alternatively, the knee prosthesis may include a "mobile" tibial bearing in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior stabilized knee prosthesis may be used to provide additional support and/or control at later degrees of flexion. Alternatively, if the posterior cruciate ligament is intact, a cruciate-retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue on the orthopaedic components may cause unwanted or undesirable motion of the orthopaedic knee prosthesis. For example, the orthopaedic knee prosthesis may exhibit an amount of unnatural (paradoxical) anterior translation (i.e., the point of contact between the femoral component and the tibial bearing moves anteriorly) as the femoral component is moved through the range of flexion relative to the tibial bearing. This paradoxical anterior translation may result in loss of joint stability, accelerated wear, abnormal knee kinematics, and/or cause the patient to experience a sensation of instability during some activities.

SUMMARY

According to one aspect, an orthopaedic knee prosthesis may include a femoral component and a tibial bearing. In some embodiments, the femoral component may be embodied as a posterior cruciate-retaining femoral component. The femoral component may include a condyle surface curved in the sagittal plane. The tibial bearing may include a bearing surface configured to articulate with the condyle surface of the femoral component. In some embodiments, the condyle surface of the femoral component may contact the bearing surface at a first contact point on the condyle surface at a first degree of flexion and contact the bearing surface at a second contact point on the condyle surface at a second degree of flexion. The first degree of flexion may be less than about 30 degrees. For example, the first degree of flexion may be in the range of 0 degrees to 10 degrees. The second degree of flexion may be in the range of 45 degrees to 90 degrees. For example, the second degree of flexion may be in the range of 60 degrees to 90 degrees. In one particular embodiment, the first degree of flexion is about 5 degrees and the second degree of flexion is about 65 degrees.

The condyle surface in the sagittal plane of the femoral component may include a first radius of curvature at the first contact point and a second radius of curvature at the second contact point. In some embodiments, the ratio of the first radius of curvature to the second radius of curvature may be in the range of 1.10 to 1.45. For example, in one particular embodiment, the ratio of the first radius of curvature to the second radius of curvature is about 1.35.

In some embodiments, the condyle surface in the sagittal plane may also contact the bearing surface at a third contact point on the condyle surface at a third degree of flexion. The third degree of flexion may be greater than the second degree of flexion. For example, the third degree of flexion may be in the range of 80 degrees to 110 degrees. In one particular embodiment, the third degree of flexion is about 90 degrees.

The condyle surface in the sagittal plane may also include a third radius of curvature at the third contact point. The third radius of curvature may be greater than the second radius of curvature by at least 0.5 millimeters. The ratio of the first radius of curvature to the third radius of curvature may be in the range of 1.10 to 1.45 and may be less than the ratio of the first radius of curvature to the second radius of curvature. For example, in one particular embodiment, the radius of curvature is about 1.28.

Additionally, in some embodiments, the condyle surface may contact the bearing surface at a fourth contact point on the condyle surface at a fourth degree of flexion. The fourth degree of flexion may be greater than the third degree of flexion. For example, the fourth degree of flexion may be in the range of 90 degrees to 120 degrees. In one particular embodiment, the third degree of flexion is about 105 degrees.

The condyle surface in the sagittal plane may also include a fourth radius of curvature at the fourth contact point. The fourth radius of curvature may be less than the third radius of curvature. The ratio of the first radius of curvature to the fourth radius of curvature may be in the range of 1.10 to 1.45. For example, in one particular embodiment, the radius of curvature is about 1.305.

Further, in some embodiments, the condyle surface may contact the bearing surface at a plurality of contact points between the first contact point and the second contact point when the femoral component is moved from the first degree of flexion to the second degree of flexion. Each contact point of the plurality of contact points may be defined by a ray extending from a common origin to the respective contact point of the plurality of contact points. Each ray may have a length defined by the equation: $r_\theta=(a+(b*\theta)+(c*\theta^2)+(d*\theta^3))$, wherein $r_\theta$ is the length of the ray defining a contact point at $\theta$ degrees of flexion, a is a coefficient value between 20 and 50, and b is a coefficient value in a range selected from the group consisting of: $-0.30<b<0.0$, $0.00<b<0.30$, and $b=0$. If b is in the range of $-0.30<b<0.00$, then c is a coefficient value between 0.00 and 0.012 and d is a coefficient value between $-0.00015$ and 0.00. Alternatively, if b is in the range of $0<b<0.30$, then c is a coefficient value between $-0.010$ and 0.00 and d is a coefficient value between $-0.00015$ and 0.00. Alternatively still, if b is equal to 0, then c is a coefficient value in a range selected from the group consisting of: $-0.0020<c<0.00$ and $0.00<c<0.0025$ and d is a coefficient value between $-0.00015$ and 0.00. In some embodiments, the distance between the origin of the first radius of curvature and the common origin of the rays is in the range of 0 and 10 millimeters.

In some embodiments, the condyle surface of the femoral component in the sagittal plane may include first curved surface section and a second curved surface section. The first curved surface section may be defined between the second contact point and the third contact point. The second curved surface section may be defined between the third contact point and the fourth contact point. In such embodiments, the first curved surface section may have a substantially constant radius of curvature substantially equal to the third radius of curvature. Additionally, the second curved surface section may have a substantially constant radius of curvature substantially equal to the fourth radius of curvature.

According to another aspect, an orthopaedic knee prosthesis may include a femoral component and a tibial bearing. In some embodiments, the femoral component may be embodied as a posterior cruciate-retaining femoral component. The femoral component may include a condyle surface curved in the sagittal plane. The tibial bearing may include a bearing surface configured to articulate with the condyle surface of the femoral component. In some embodiments, the condyle surface of the femoral component may contact the bearing surface at a first contact point on the condyle surface at a first degree of flexion, contact the bearing surface at a second contact point on the condyle surface at a second degree of flexion, and contact the bearing surface at a plurality of contact points between the first contact point and the second contact point when the femoral component is moved from the first degree of flexion to the second degree of flexion. The first degree of flexion may be less than about 30 degrees. For example, the first degree of flexion may be in the range of 0 degrees to 10 degrees. The second degree of flexion may in the range of 45 degrees to 90 degrees. For example, the second degree of flexion may be in the range of 60 degrees to 90 degrees. In one particular embodiment, the first degree of flexion is about 5 degrees and the second degree of flexion is about 65 degrees.

Each contact point of the plurality of contact points may be defined by a ray extending from a common origin to the respective contact point of the plurality of contact points. Each ray may have a length defined by the equation: $r_\theta=(a+(b*\theta)+(c*\theta^2)+(d*\theta^3))$, wherein $r_\theta$ is the length of the ray defining a contact point at $\theta$ degrees of flexion, a is a coefficient value between 20 and 50, and b is a coefficient value in a range selected from the group consisting of: $-0.30<b<0.0$, $0.00<b<0.30$, and $b=0$. If b is in the range of $-0.30<b<0.00$, then c is a coefficient value between 0.00 and 0.012 and d is a coefficient value between $-0.00015$ and 0.00. Alternatively, if b is in the range of $0<b<0.30$, then c is a coefficient value between $-0.010$ and 0.00 and d is a coefficient value between $-0.00015$ and 0.00. Alternatively still, if b is equal to 0, then c is a coefficient value in a range selected from the group consisting of: $-0.0020<c<0.00$ and $0.00<c<0.0025$ and d is a coefficient value between $-0.00015$ and 0.00. In some embodiments, the distance between the origin of the first radius of curvature and the common origin of the rays is in the range of 0 and 10 millimeters.

Additionally, in some embodiments, the condyle surface may contact the bearing surface at a third contact point on the condyle surface at a third degree of flexion and may contact the bearing surface at a fourth contact point on the condyle surface at a fourth degree of flexion. The third degree of flexion may be greater than the second degree of flexion and the fourth degree of flexion may be greater than the third degree of flexion. The condyle surface in the sagittal plane may include a first radius of curvature at the first contact point, a second radius of curvature at the second contact point, a third radius of curvature at the third contact point, and a fourth radius of curvature at the fourth contact point. The ratio of the first radius of curvature to the third radius of curvature may be less than the ratio of the first radius of curvature to the second radius of curvature. Additionally, the ratio of the first radius of curvature to the third radius of curvature may be less than the ratio of the first radius of curvature to the fourth radius of curvature. For example, in one particular embodiment, the ratio of the first radius of curvature to the second radius of curvature is about 1.35, the ratio of the first radius of curvature to the third radius of curvature is about 1.28, and the ratio of the first radius of curvature to the third radius of curvature is about 1.305.

Further, in some embodiments, the condyle surface of the femoral component in the sagittal plane may include first curved surface section and a second curved surface section. The first curved surface section may be defined between the second contact point and the third contact point. The second curved surface section may be defined between the third contact point and the fourth contact point. In such embodiments, the first curved surface section may have a substantially constant radius of curvature substantially equal to the third radius of curvature. Additionally, the second curved surface section may have a substantially constant radius of curvature substantially equal to the fourth radius of curvature.

According to a further aspect, an orthopaedic knee prosthesis may include a femoral component and a tibial bearing. The femoral component may include a condyle surface curved in the sagittal plane. The tibial bearing may include a bearing surface configured to articulate with the condyle surface of the femoral component. In some embodiments, the condyle surface of the femoral component may contact the bearing surface at a first contact point on the condyle surface at a first degree of flexion, contact the bearing surface at a second contact point on the condyle surface at a second degree of flexion, contact the bearing surface at a third contact point on the condyle surface at a third degree of flexion, and contact the bearing surface at a plurality of contact points between the first contact point and the second contact point when the femoral component is moved from the first degree of flexion to the second degree of flexion. The first degree of flexion may be less than about 30 degrees, the second degree of flexion may be in the range of 45 degrees to 90 degrees, and the third degree of flexion may be greater than the second degree of flexion.

The condyle surface in the sagittal plane of the femoral component may include a first radius of curvature at the first contact point, a second radius of curvature at the second contact point, and a third radius of curvature at the third contact point. The ratio of the first radius of curvature to the second radius of curvature may be in the range of 1.10 to 1.45. The ratio of the first radius of curvature to the third radius of curvature may be less than the ratio of the first radius of curvature to the second radius of curvature and may be in the range of 1.10 to 1.45.

Each contact point of the plurality of contact points may be defined by a ray extending from a common origin to the respective contact point of the plurality of contact points. Each ray may have a length defined by the equation: $r_\theta=(a+(b*\theta)+(c*\theta^2)+(d*\theta^3))$, wherein $r_\theta$ is the length of the ray defining a contact point at $\theta$ degrees of flexion, a is a coefficient value between 20 and 50, and b is a coefficient value in a range selected from the group consisting of: $-0.30<b<0.0$, $0.00<b<0.30$, and $b=0$. If b is in the range of $-0.30<b<0.00$, then c is a coefficient value between 0.00 and 0.012 and d is a coefficient value between $-0.00015$ and 0.00. Alternatively, if b is in the range of $0<b<0.30$, then c is a coefficient value between $-0.010$ and 0.00 and d is a coefficient value between $-0.00015$ and 0.00. Alternatively still, if b is equal to 0, then c is a coefficient value in a range selected from the group consisting of: $-0.0020<c<0.00$ and $0.00<c<0.0025$ and d is a coefficient value between $-0.00015$ and 0.00. In some embodiments, the distance between the origin of the first radius of curvature and the common origin of the rays is in the range of 0 and 10 millimeters.

Additionally, in some embodiments, each of the pair of spaced apart condyles may include a condyle surface. In such embodiments, the condyle surfaces may be substantially symmetrical or may be asymmetrical.

BRIEF DESCRIPTION OF THE DRAWINGS

The detailed description particularly refers to the following figures, in which:

FIG. 10 is a table of one embodiment of radii of curvature length values and ratio for a family of femoral component sizes;

FIG. 12 is a table of one embodiment of coefficient values of a polynomial equation defining a curve of the femoral component of FIG. 1 for a family of femoral component sizes.

DETAILED DESCRIPTION OF THE DRAWINGS

Figure 1:
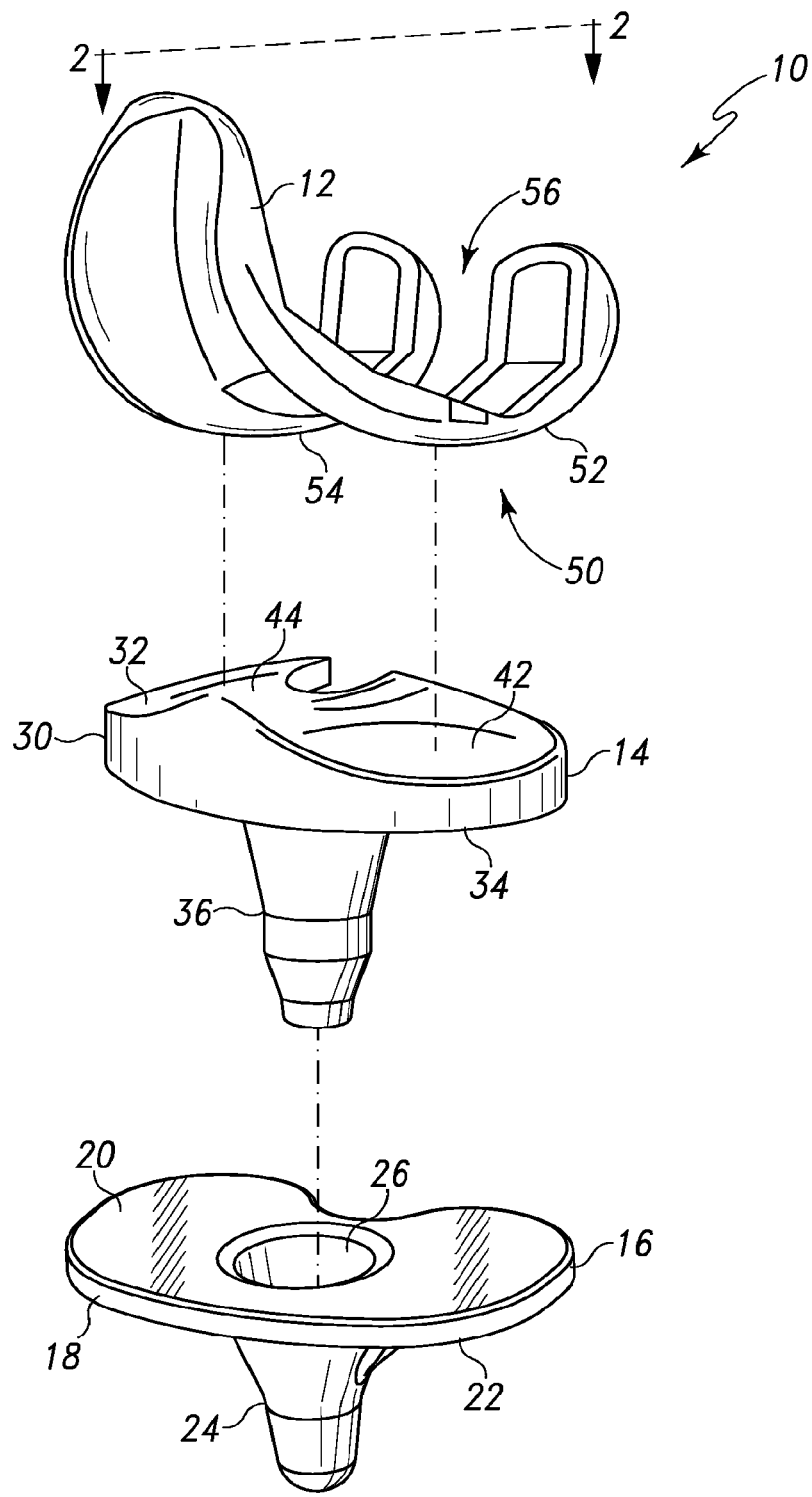
FIG. 1 is an exploded perspective view of one embodiment of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior cruciate-retaining orthopaedic knee prosthesis 10 includes a femoral component 12, a tibial bearing 14, and a tibial tray 16. The femoral component 12 and the tibial tray 16 are illustratively formed from a metallic material such as cobalt-chromium or titanium, but may be formed from other materials, such as a ceramic material, a polymer material, a bio-engineered material, or the like, in other embodiments. The tibial bearing 14 is illustratively formed from a polymer material such as a ultra-high molecular weight polyethylene (UHMWPE), but may be formed from other materials, such as a ceramic material, a metallic material, a bio-engineered material, or the like, in other embodiments.

As discussed in more detail below, the femoral component 12 is configured to articulate with the tibial bearing 14, which is configured to be coupled with the tibial tray 16. The illustrative tibial bearing 14 is embodied as a rotating or mobile tibial bearing and is configured to rotate relative to the tibial tray 12 during use. However, in other embodiments, the tibial bearing 14 may be embodied as a fixed tibial bearing, which may be limited or restricted from rotating relative the tibial tray 16.

The tibial tray 16 is configured to be secured to a surgically-prepared proximal end of a patient's tibia (not shown). The tibial tray 16 may be secured to the patient's tibia via use of bone adhesive or other attachment means. The tibial tray 16 includes a platform 18 having an top surface 20 and a bottom surface 22. Illustratively, the top surface 20 is generally planar and, in some embodiments, may be highly polished. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem of the tibial insert 14 as discussed in more detail below.

As discussed above, the tibial bearing 14 is configured to be coupled with the tibial tray 16. The tibial bearing 14 includes a platform 30 having an upper bearing surface 32 and a bottom surface 34. In the illustrative embodiment wherein the tibial bearing 14 is embodied as a rotating or mobile tibial bearing, the bearing 14 includes a stem 36 extending downwardly from the bottom surface 32 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 22 and/or may include other devices or features to secure the tibial bearing 14 to the tibial tray 12 in a non-rotating configuration.

The upper bearing surface 32 of the tibial bearing 14 includes a medial bearing surface 42 and a lateral bearing surface 44. The medial and lateral bearing surfaces 42, 44 are configured to receive or otherwise contact corresponding medial and lateral condyles of the femoral component 14 as discussed in more detail below. As such, each of the bearing surface 42, 44 has a concave contour.

The femoral component 12 is configured to be coupled to a surgically-prepared surface of the distal end of a patient's femur (not shown). The femoral component 12 may be secured to the patient's femur via use of bone adhesive or other attachment means. The femoral component 12 includes an outer, articulating surface 50 having a pair of medial and lateral condyles 52, 54. The condyles 52, 54 are spaced apart to define an intracondyle opening 56 therebetween. In use, the condyles 52, 54 replace the natural condyles of the patient's femur and are configured to articulate on the corresponding bearing surfaces 42, 44 of the platform 30 of the tibial bearing 14.

It should be appreciated that the illustrative orthopaedic knee prosthesis 10 is configured to replace a patient's right knee and, as such, the bearing surface 42 and the condyle 52 are referred to as being medially located; and the bearing surface 44 and the condyle 54 are referred to as being laterally located. However, in other embodiments, the orthopaedic knee prosthesis 10 may be configured to replace a patient's left knee. In such embodiments, it should be appreciated the bearing surface 42 and the condyle 52 may be laterally located and the bearing surface 44 and the condyle 54 may be medially located. Regardless, the features and concepts described herein may be incorporated in an orthopaedic knee prosthesis configured to replace either knee joint of a patient.

Figure 2:
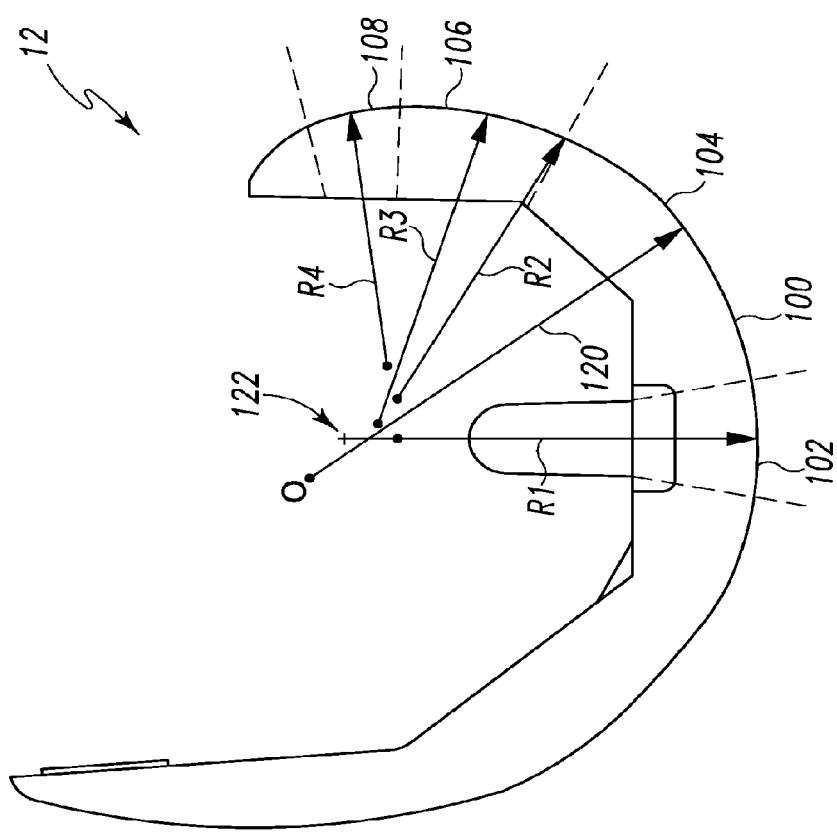
FIG. 2 is a cross-sectional view of one embodiment of a femoral component of the orthopaedic prosthesis of FIG. 1 taken generally along section line 2-2.
Figure 3:
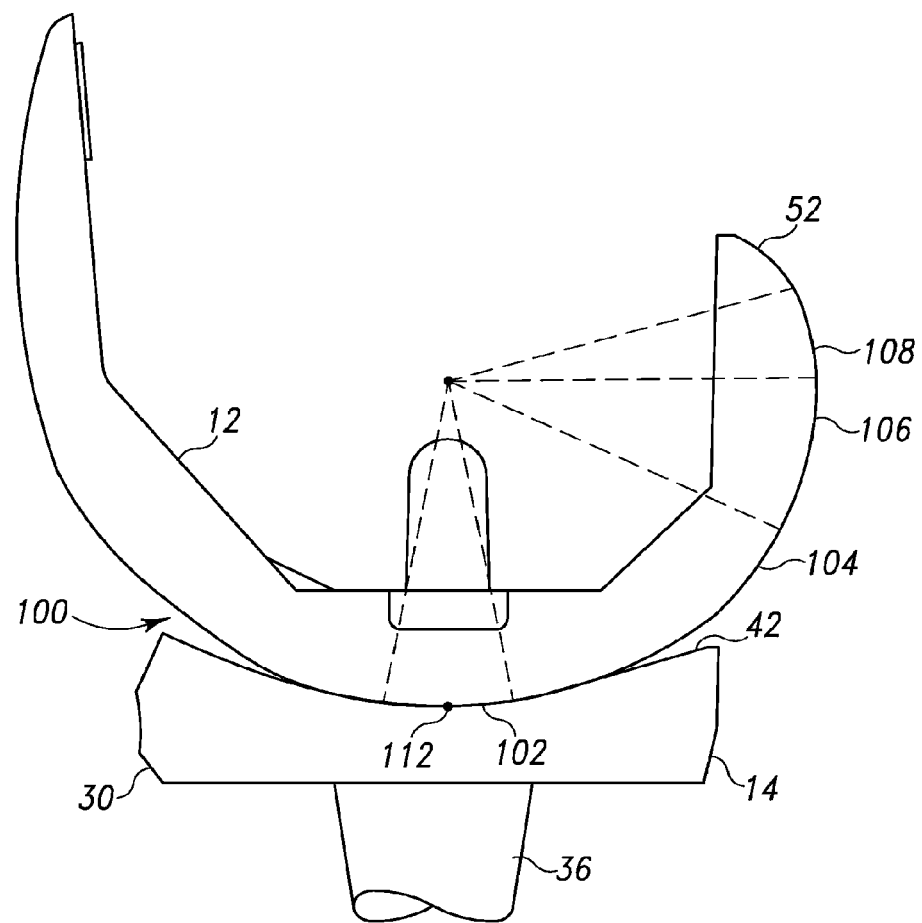
FIG. 3 is a cross-sectional view of the femoral component of FIG. 2 positioned on a tibial bearing of the orthopaedic prosthesis of FIG. 1 at about zero degrees of flexion.

Referring now to FIG. 2, each of the condyles 52, 54 of the femoral component 12 includes a condyle surface 100, which is convexly curved in the sagittal plane. The condyle surface 100 is formed from a number of curved surface sections 102, 104, 106, and 108, each of which is tangent to the adjacent curved surface section. Each curved surface sections 102, 104, 106, and 108 contacts the tibial bearing 14 through different ranges of degrees of flexion. For example, the curved surface sections 102, 104 of the condyle surface 100 contact the tibial bearing 14 during early flexion. That is, as the femoral component 12 is articulated through the early degrees of flexion relative to the tibial bearing 14, the femoral component 12 contacts the tibial bearing 14 at one or more contact points on the curved surface section 102 or the curved surface section 104 at each degree of early flexion. For example, as illustrated in FIG. 3, when the femoral component 12 is positioned at about 0 degrees of flexion, the femoral component 12 contacts the bearing surface 42 of the tibial bearing 14 at a contact point 112 on the condyle surface 100.

Figure 4:
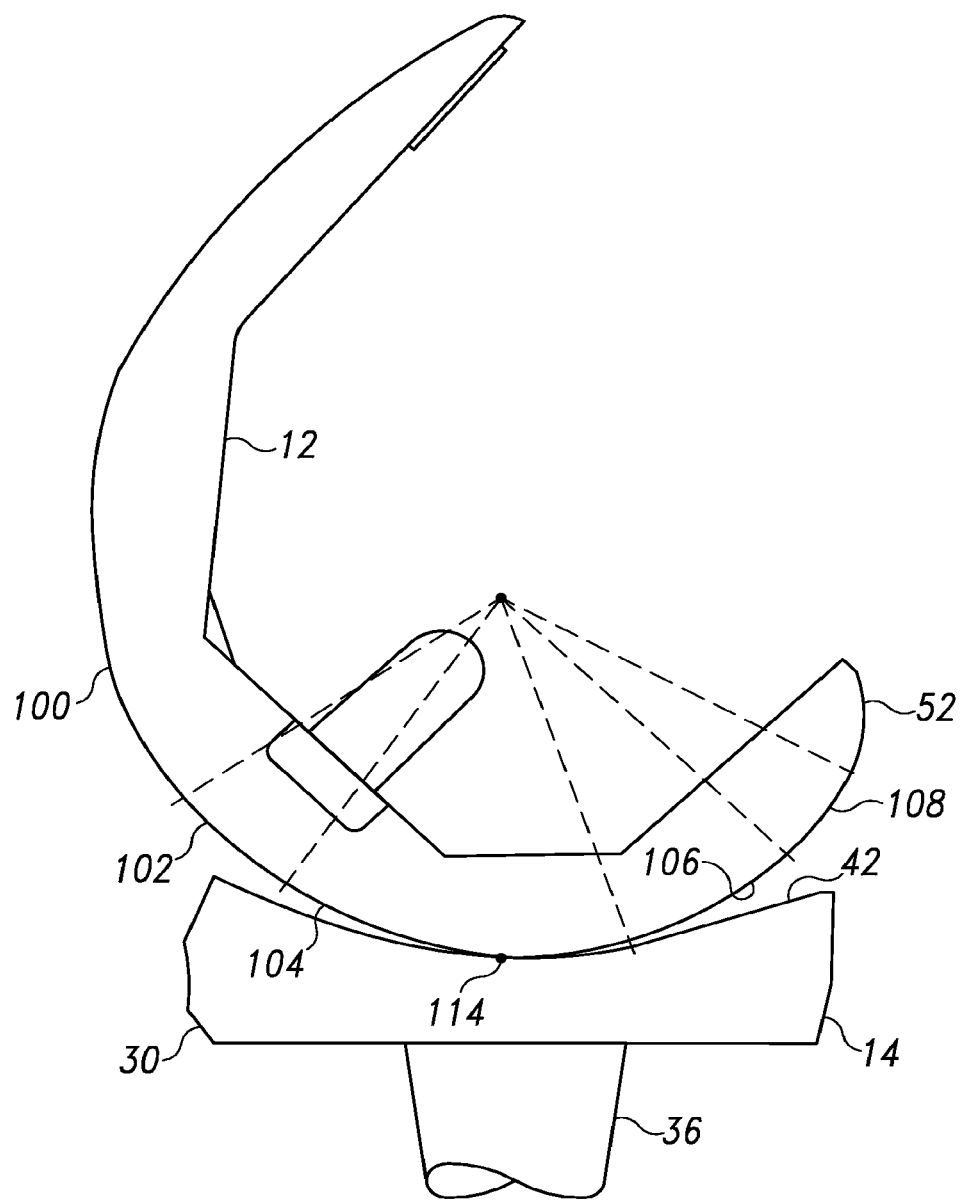
FIG. 4 is a cross-sectional view of the femoral component and tibial bearing of FIG. 3 positioned at about 45 degrees of flexion.
Figure 5:
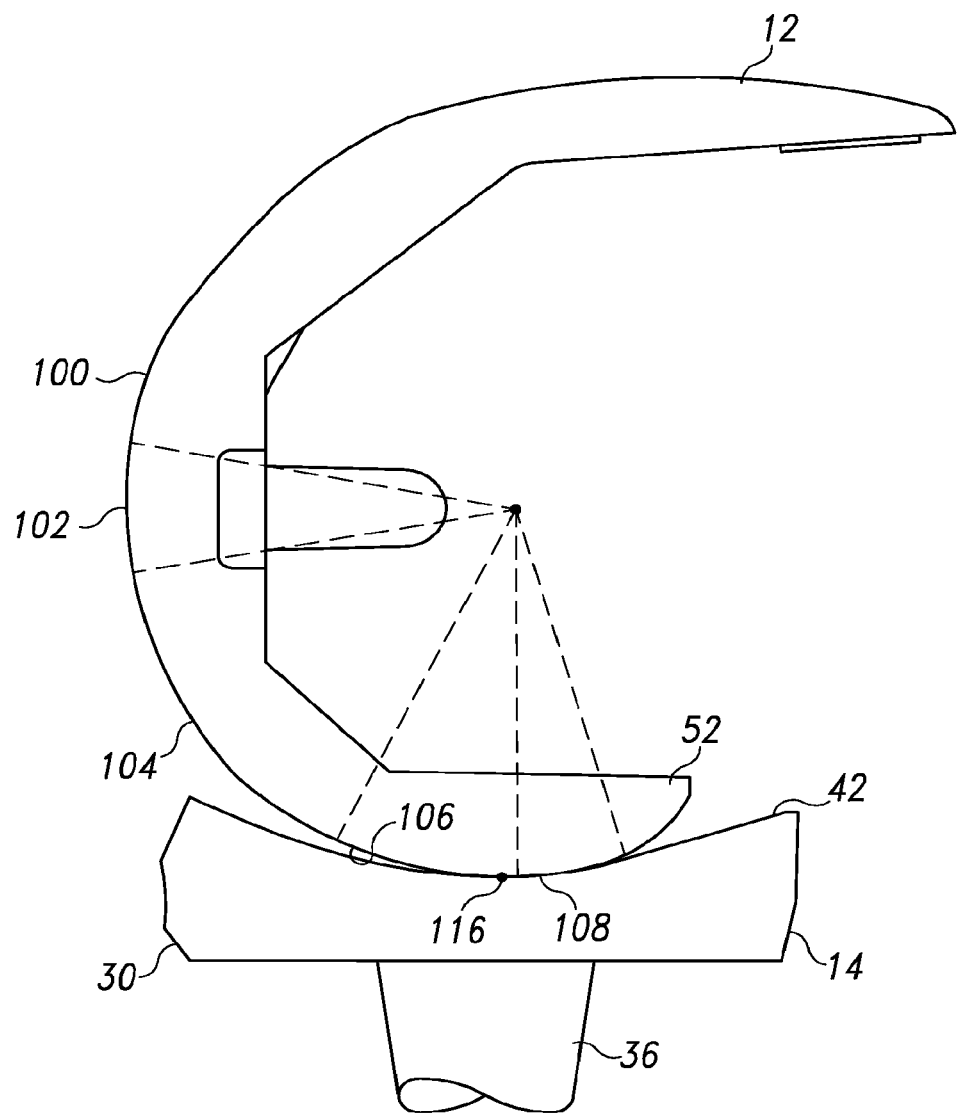
FIG. 5 is a cross-sectional view of the femoral component and tibial bearing of FIG. 3 positioned at about 90 degrees of flexion.

Similarly, the curved surface section 104 of the condyle surface 100 contacts the tibial bearing 14 during mid flexion; and the curved surface section 106 of the condyle surface 100 contacts the tibial bearing 14 during late flexion. As the femoral component 12 is articulated through the middle degrees of flexion relative to the tibial bearing 14, the femoral component 12 contacts the tibial bearing 14 at one or more contact points on the curved surface section 104 at each degree of mid flexion. For example, as illustrated in FIG. 4, when the femoral component 12 is positioned at about 45 degrees of flexion, the femoral component 12 contacts the bearing surface 42 of the tibial bearing 14 at a contact point 114 on the condyle surface 100. Additionally, as the femoral component 12 is articulated through the late degrees of flexion relative to the tibial bearing 14, the femoral component 12 contacts the tibial bearing 14 at one or more contact points on the curved surface section 106 at each degree of late flexion. For example, as illustrated in FIG. 5, when the femoral component 12 is positioned at about 90 degrees of flexion, the femoral component 12 contacts the bearing surface 42 of the tibial bearing 14 at a contact point 116 on the condyle surface 100. Of course, it should be appreciated that the femoral component 12 contacts the tibial bearing 14 at a plurality of contact points on the condyle surface 100 at any one particular degree of flexion. However, for clarity of description, only the contact points 112, 114, 116 have been illustrated in FIGS. 3-5, respectively.

Referring back to FIG. 2, each of the curved surface sections 102, 106, 108 of the condyle surface 100 is defined by a constant radius of curvature R1, R3, R4, respectively. However, as discussed in more detail below, the curved surface section 104 is defined by a plurality of rays, rather than a constant radius of curvature. As discussed in more detail below, the curved surface section 104 is designed to gradually transition the condyle surface 100 from the radius of curvature R1 of the curved surface section 102 to a radius of curvature R2, which is tangent to the curved surface section 106.

The curved surface sections 102, 104, 106, 108 are designed such that the amount of paradoxical anterior translation of the femoral component 12 relative to the tibial bearing 14 is reduced or otherwise delayed to a larger degree of flexion. It should be appreciated that by delaying the onset of any paradoxical anterior translation of the femoral component to a larger degree of flexion, the overall occurrence of the paradoxical anterior translation may be reduced during those activities of a patient in which deep flexion is not typically obtained.

In a typical orthopaedic knee prosthesis, paradoxical anterior translation may occur whenever the knee prosthesis is positioned at a degree of flexion greater than zero degrees.

The likelihood of anterior translation increases as the orthopaedic knee prosthesis is articulated to larger degrees of flexion. In such orientations, paradoxical anterior translation of the femoral component on the tibial bearing can occur whenever the tangential (traction) force between the femoral component and the tibial bearing fails to satisfy the following equation:

$$T < \mu N \qquad (1)$$

wherein "T" is the tangential (traction) force, "$\mu$" is the coefficient of friction of the femoral component and the tibial bearing, and "N" is the normal force between the femoral component and the tibial bearing. As a generalization, the tangential (traction) force between the femoral component and the tibial bearing can be defined as $$T = M/R \qquad (2)$$

wherein "T" is the tangential (traction) force between the femoral component and the tibial bearing, "M" is the knee moment, and "R" is the radius of curvature in the sagittal plane of the condyle surface in contact with the tibial bearing at the particular degree of flexion. It should be appreciated that equation (2) is a simplification of the governing real-world equations, which does not consider such other factors as inertia and acceleration. Regardless, the equation (2) provides insight that paradoxical anterior translation of an orthopaedic knee prosthesis may be reduced or delayed by controlling the radius of curvature of the condyle surface of the femoral component. That is, by controlling the radius of curvature of the condyle surface (e.g., increasing or maintaining the radius of curvature), the right-hand side of equation (2) may be reduced, thereby decreasing the value of the tangential (traction) force and satisfying the equation (1). As discussed above, by ensuring that the tangential (traction) force satisfies equation (1), paradoxical anterior translation of the femoral component on the tibial bearing may be reduced or otherwise delayed to a greater degree of flexion.

Based on the above analysis, one way to reduce or delay paradoxical anterior translation of the femoral component 12 is to ensure that the change in the radius of curvature of the condyle surface 100 in the early and mid flexion ranges is not too great or too abrupt (e.g., the ratio of the degree of change in radius of curvature to the change in degrees of flexion is too great). That is, if the ratio of the radius of curvature R1 to the radius of curvature R2, R3, or R4 is too great, paradoxical anterior translation of the femoral component 12 may occur. As such, by designing the condyle surface 100 of the femoral component 12 such that the ratios of the radius of curvature R1 of the early flexion curved surface section 102 to (i) the radius of curvature R2 of the early flexion curved surface section 104, (ii) the radius of curvature R3 of the mid flexion curved surface section 106, and (iii) the radius of curvature R4 of the late flexion curved surface section 108 are less than a predetermined threshold value, paradoxical anterior sliding may unexpectedly be reduced or otherwise delayed.

Accordingly, in one embodiment, the condyle surface 100 of the femoral component 12 is designed such that the ratios of the radius of curvature of R1 to the radius of curvature of (i) R2, (ii) R3, and (iii) R4 are each between about 1.10 and about 1.45. In one particular embodiment, the condyle surface 100 is designed such that the ratio of the radius of curvature of R1 to the radius of curvature of R2 is between about 1.30 and about 1.40, and in another particular embodiment, is about 1.35. Additionally, in one particular embodiment, the condyle surface 100 is designed such that the ratio of the radius of curvature of R1 to the radius of curvature of R3 is between about 1.20 and about 1.30 and, in another particular embodiment, is about 1.28. Further, in one particular embodiment, the condyle surface 100 is designed such that the ratio of the radius of curvature of R1 to the radius of curvature of R4 is between about 1.25 and about 1.35 and, in another particular embodiment, is about 1.305.

Additionally, based on the above analysis in regard to equations (1) and (2), another way to reduce or delay paradoxical anterior translation of the femoral component 12 is to increase the radius of curvature of the condyle surface 100 during early and/or mid flexion. As such, in one embodiment, the condyle surface 100 of the femoral component 12 is designed such that the radius of curvature R3 of the curved surface section 106 is greater than the radius of curvature R2 of the curved surface section 104.

The amount of increase between the radius of curvature R2 and the radius of curvature R3, as well as, the degree of flexion on the condyle surface 100 at which such increase occurs has been determined to affect the occurrence of paradoxical anterior translation. As discussed in more detail in the U.S. patent application Ser. No. 12/165,579, entitled "Orthopaedic Femoral Component Having Controlled Condylar Curvature", which was filed concurrently herewith and is hereby incorporated by reference, multiple simulations of various femoral component designs were performed using the LifeMOD/Knee Sim, version 2007.1.0 Beta 16 software program, which is commercially available from LifeModeler, Inc. of San Clemente, Calif., to analyze the effect of increasing the radius of curvature of the condyle surface of the femoral components in early and mid flexion. Based on such analysis, it has been determined that paradoxical anterior sliding of the femoral component relative to the tibial bearing may be reduced or otherwise delayed by increasing the radius of curvature of the condyle surface by an amount in the range of about 0.5 millimeters to about 5 millimeters at a degree of flexion in the range of about 30 degrees of flexion to about 90 degrees of flexion.

Figure 6:
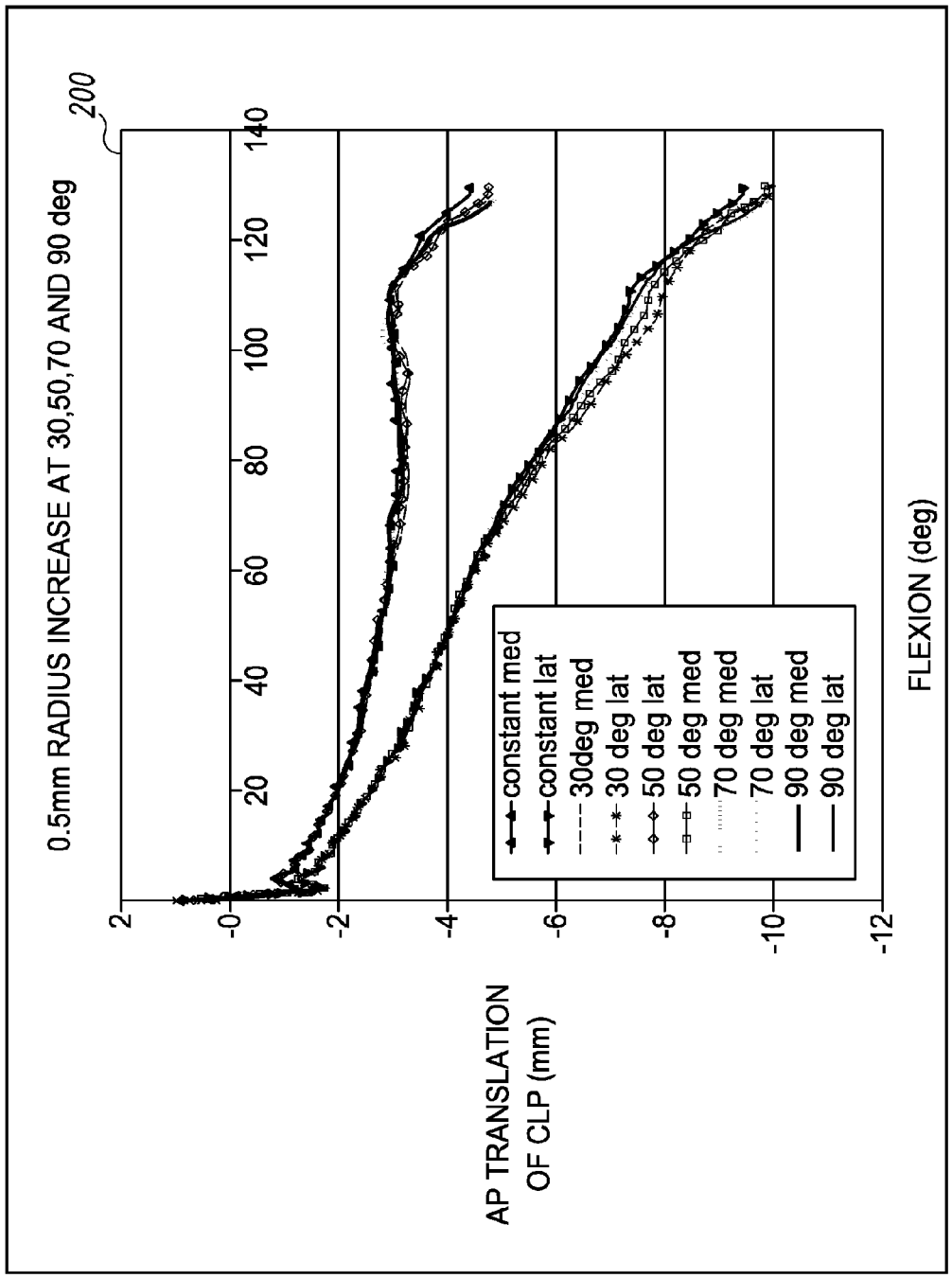
FIG. 6 is graph of the anterior-posterior translation of a simulated femoral component having an increased radius of curvature located at various degrees of flexion.
Figure 7:
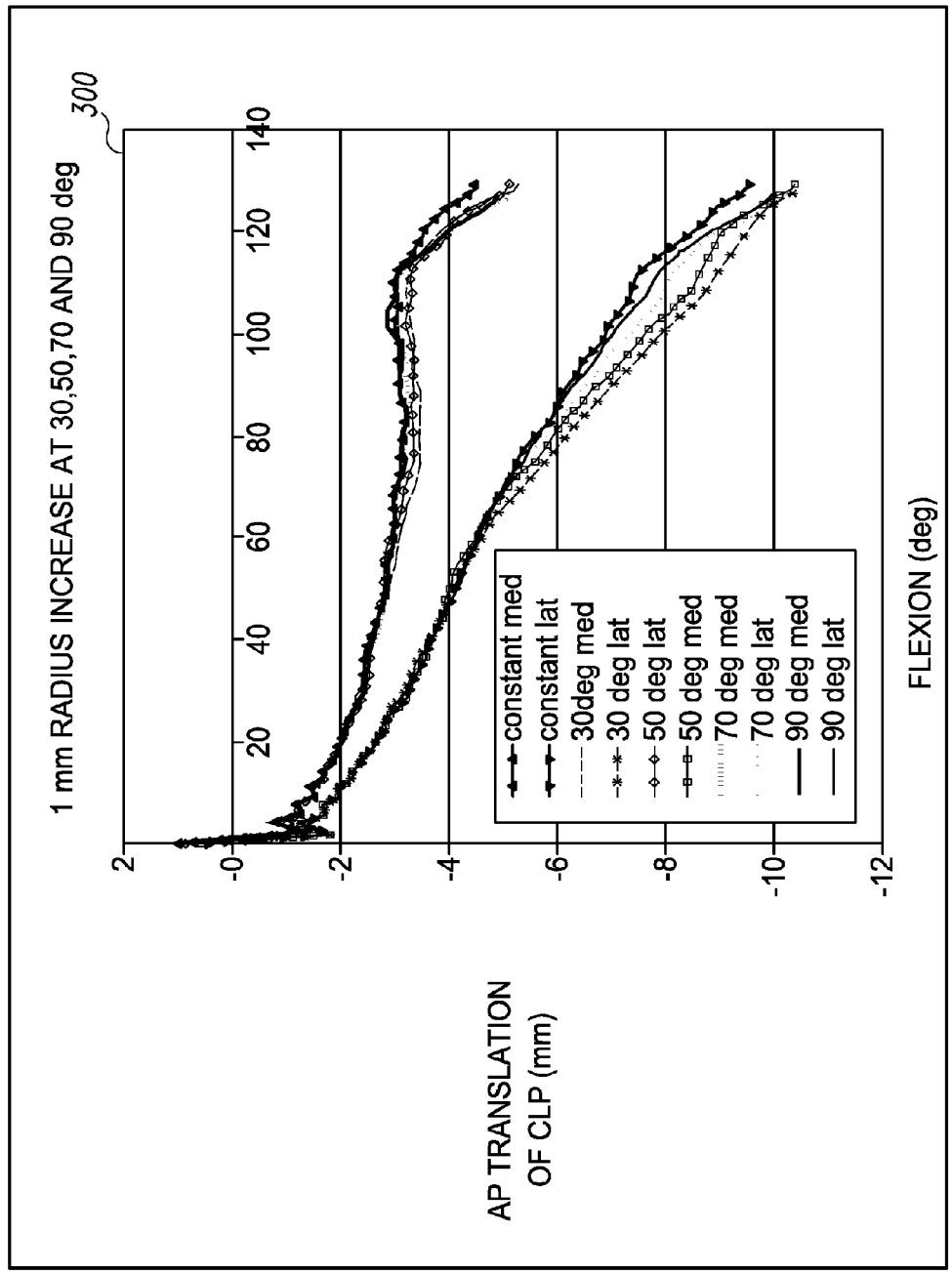
FIG. 7 is graph of the anterior-posterior translation of another simulated femoral component having an increased radius of curvature located at various degrees of flexion.
Figure 8:
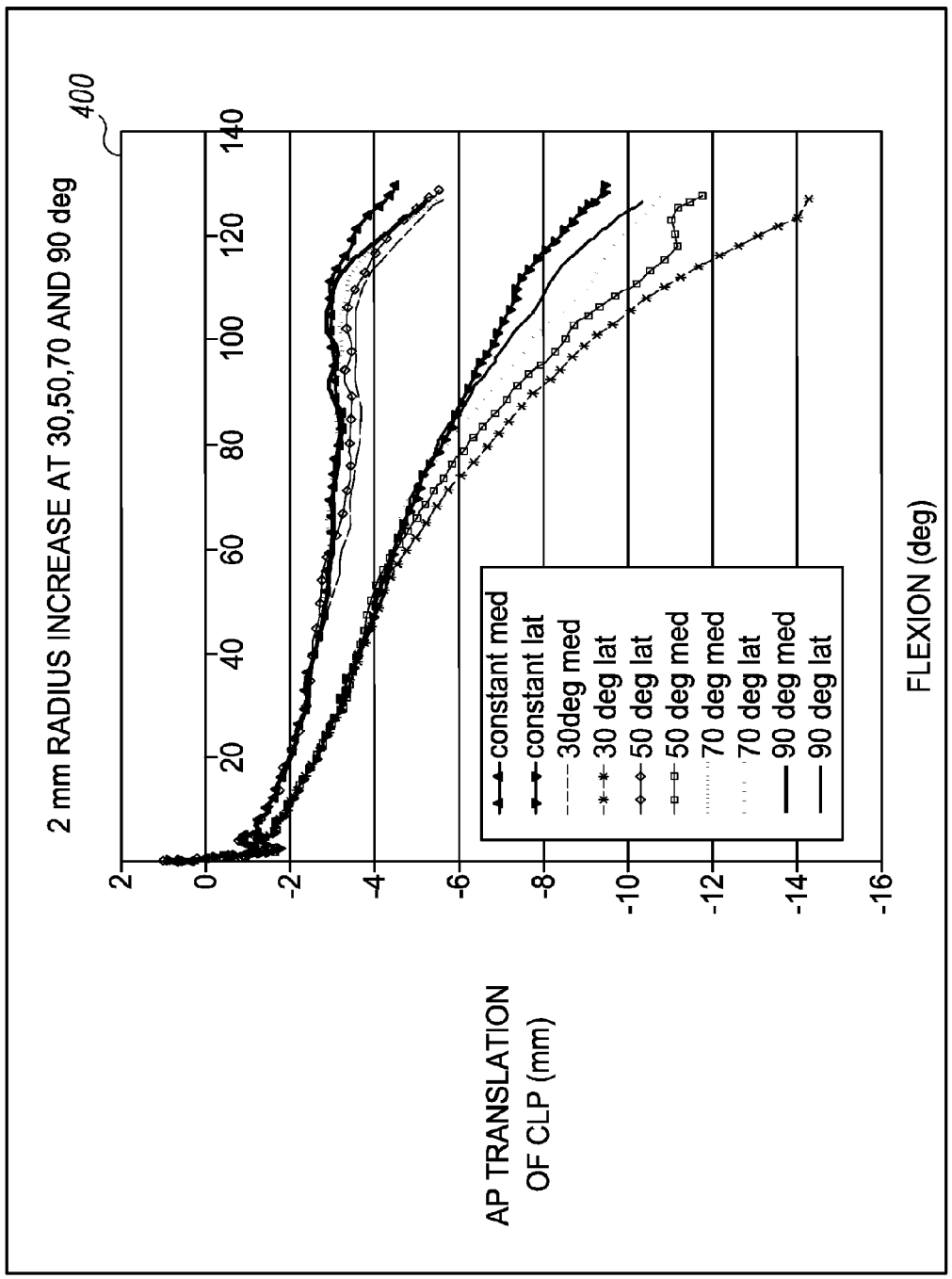
FIG. 8 is graph of the anterior-posterior translation of another simulated femoral component having an increased radius of curvature located at various degrees of flexion.
Figure 9:
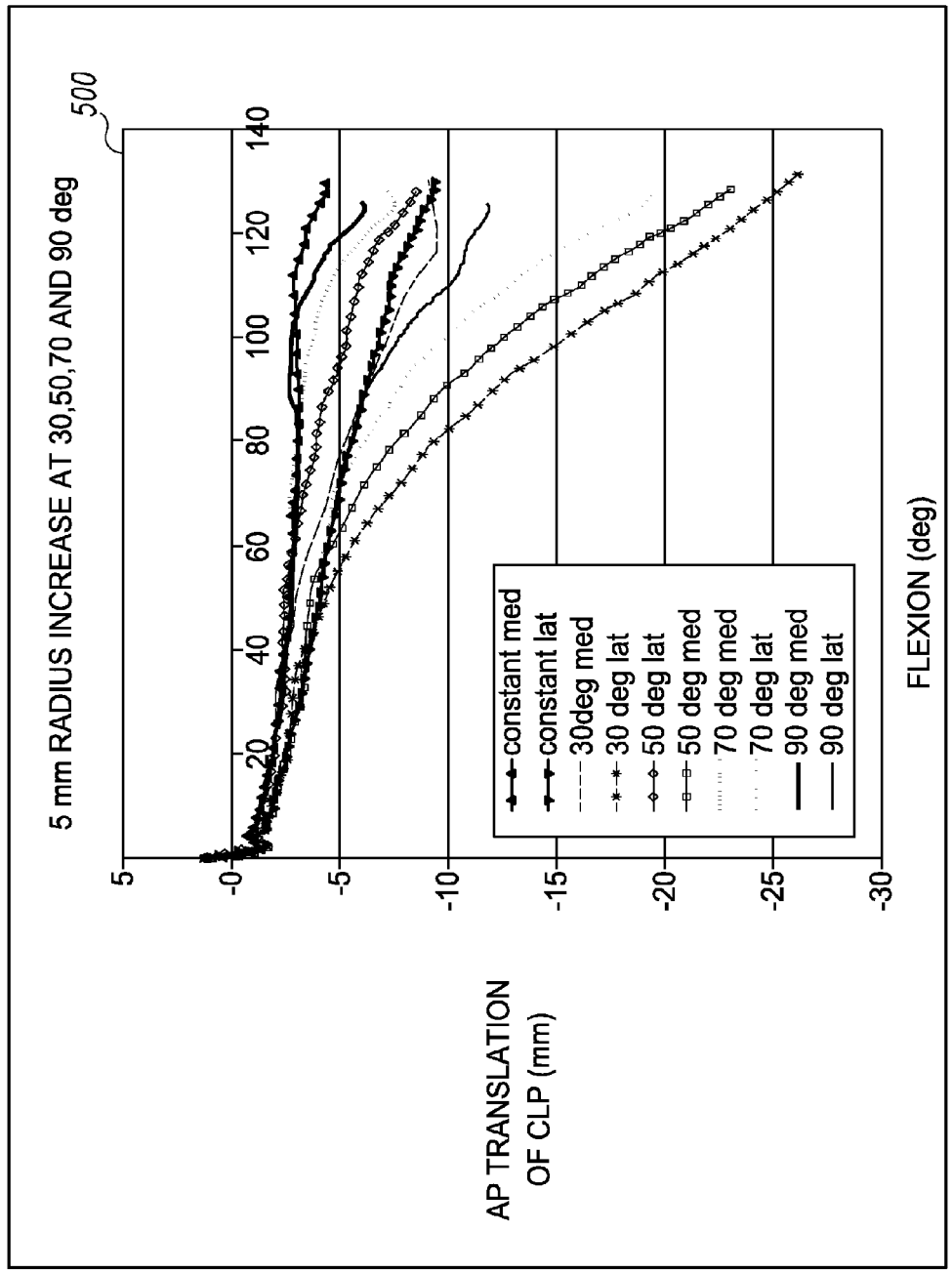
FIG. 9 is graph of the anterior-posterior translation of another simulated femoral component having an increased radius of curvature located at various degrees of flexion.

For example, the graph 200 illustrated in FIG. 6 presents the results of a deep bending knee simulation using a femoral component wherein the radius of curvature of the condyle surface is increased by 0.5 millimeters (i.e., from 25.0 millimeters to 25.5 millimeters) at 30 degrees of flexion, at 50 degrees of flexion, at 70 degrees of flexion, and at 90 degrees of flexion. Similarly, the graph 300 illustrated in FIG. 7 presents the results of a deep bending knee simulation using a femoral component wherein the radius of curvature of the condyle surface is increased by 1.0 millimeters (i.e., from 25.0 millimeters to 26.0 millimeters) at 30 degrees of flexion, at 50 degrees of flexion, at 70 degrees of flexion, and at 90 degrees of flexion. The graph 400 illustrated in FIG. 8 presents the results of a deep bending knee simulation using a femoral component wherein the radius of curvature of the condyle surface is increased by 2.0 millimeters (i.e., from 25.0 millimeters to 27.0 millimeters) at 30 degrees of flexion, at 50 degrees of flexion, at 70 degrees of flexion, and at 90 degrees of flexion. Additionally, the graph 500 illustrated in FIG. 9 presents the results of a deep bending knee simulation using a femoral component wherein the radius of curvature of the condyle surface is increased by 5.0 millimeters (i.e., from 25.0 millimeters to 26.0 millimeters) at 30 degrees of flexion, at 50 degrees of flexion, at 70 degrees of flexion, and at 90 degrees of flexion.

In the graphs 200, 300, 400, 500, the condylar lowest or most distal points (CLP) of the medial condyle ("med") and the lateral condyle ("lat") of the femoral component are graphed as a representation of the relative positioning of the femoral component to the tibial bearing. As such, a downwardly sloped line represents roll-back of the femoral component on the tibial bearing and an upwardly sloped line represents anterior translation of the femoral component on the tibial bearing.

As illustrated in the graphs 200, 300, 400, 500, anterior sliding of the femoral component was delayed until after about 100 degrees of flexion in each of the embodiments; and the amount of anterior translation was limited to less than about 1 millimeter. In particular, "roll-back" of the femoral component on the tibial bearing was promoted by larger increases in the radius of curvature of the condyle surface at earlier degrees of flexion. Of course, amount of increase in the radius of curvature and the degree of flexion at which such increase is introduced is limited by other factors such as the anatomical joint space of the patient's knee, the size of the tibial bearing, and the like. Regardless, based on the simulations reported in the graphs 200, 300, 400, 500, paradoxical anterior translation of the femoral component on the tibial bearing can be reduced or otherwise delayed by increasing the radius of curvature of the condyle surface of the femoral component during early to mid flexion.

Referring back to FIG. 2, based on the above-described analysis, the condyle surface 100 of the femoral component 12 is designed such that the radius of curvature R3 is greater than the radius of curvature R2 by an amount in the range of about 0.5 millimeters to about 5 millimeters in one embodiment. As discussed below, the particular amount of increase may be based on the size of the femoral component in some embodiments. Additionally, based on the above analysis, the condyle surface 100 is designed such that the increase in the radius of curvature from R2 to R3 occurs at a degree of flexion in the range of about 45 degrees to about 90 degrees. In one particular embodiment, the increase in radius of curvature from R2 to R3 occurs at about 65 degrees of flexion on the condyle surface 100.

As discussed above, the curved surface section 104 is designed to provide a gradual transition from the radius of curvature R1 to the radius of curvature R2. As such, the size of the angle defined by the curved surface section 104 may be selected based on the desired rate of transition. For example, in one embodiment, the condyle surface 100 of the femoral component 12 is designed such that the curved surface section 104 extends from a first degree of flexion in the range of about 0 to about 30 degrees to a second degree of flexion in the range of about 45 to about 90 degrees of flexion. In one particular embodiment, the curved surface section 104 extends from about 5 degrees of flexion to about 65 degrees of flexion. It should be appreciated that the positioning (i.e., the initial degree of flexion) and the size (i.e., the angle defined thereby) of the curved surface section 104 also determines, at least in part, the positioning and size of the early flexion curved surface section 102. As such, in one embodiment, the curved surface section 102 extends from a first degree of flexion in the range of about −10 degrees (i.e., 10 degrees of hyperextension) to about 0 degrees of flexion to a second degree of flexion in the range of about 5 degrees to about 30 degrees. In one particular embodiment, the curved surface section 102 extends from about −10 degrees of flexion to about 5 degrees of flexion.

Similarly, the positioning and size of the curved surface sections 106 and 108 are determined, at least in part, on the positioning and size of the curved surface section 104. Additionally, the positioning and size of the curved surface sections 106 and 108 are based on or otherwise limited by the anatomical restraints of the joint space of the knee. That is, the overall size and configuration of the posterior side of the condyle surface 100 of the femoral component 12 is designed such that the femoral component 12 "fits" into the joint space of a knee and allows the femoral component 12 to be properly secured to a patient's surgically-prepared distal femur. As such, in one embodiment, the curved surface section 106 extends from a first degree of flexion in the range of about 45 degrees to about 90 degrees to a second degree of flexion in the range of about 80 degrees to about 110 degrees. In one particular embodiment, the curved surface section 106 extends from about 65 degrees of flexion to about 90 degrees of flexion. Similarly, in one embodiment, the curved surface section 108 extends from a first degree of flexion in the range of about 80 degrees to about 110 degrees to a second degree of flexion in the range of about 90 degrees to about 120 degrees. In one particular embodiment, the curved surface section 106 extends from about 90 degrees of flexion to about 105 degrees of flexion.

It should be appreciated that the particular amount of increase in the radius of curvature R2 to R3 of the condyle surface 100 of the femoral component 12 and/or the positioning of such increase on the condyle surface 100 may also be based on, scaled, or otherwise affected by the size of the femoral component 12. That is, it should be appreciated that an increase of the radius of curvature R2 to R3 of the condyle surface 100 of 0.5 millimeters is a relatively larger increase in small-sized femoral components compared to larger-sized femoral components. As such, the magnitude of the increase in the radius of curvature R2 to R3 of the condyle surface 100 of the femoral component 12 may change across femoral component sizes. In one embodiment, however, the ratios of the radius of curvatures R1 to the radius of curvatures R2, R3, and R4 are maintained at a substantially constant value across the family of femoral component sizes.

For example, as illustrated in FIG. 10, a table 600 defines the length of each radius of curvature R1, R2, R3, R4 for a family of femoral component sizes 1 through 10. As illustrated in the table 600, the length of each radius of curvature R1, R2, R3, R4 for each size 1-10 of the femoral component 12 is selected such that the ratios of R1/R2, R1/R3, and R1/R4 are substantially constant across the femoral component sizes. In the illustrative embodiment, as previously discussed, the ratio of the radius of curvature R1 to the radius of curvature R2 is maintained at a value of about 1.35 across the femoral component sizes 1 through 10, the ratio of the radius of curvature R1 to the radius of curvature R3 is maintained at a value of about 1.28 across the femoral component sizes 1 through 10, and the ratio of the radius of curvature R1 to the radius of curvature R4 is maintained at a value of about 1.305 across the femoral component sizes 1 through 10.

Figure 11:
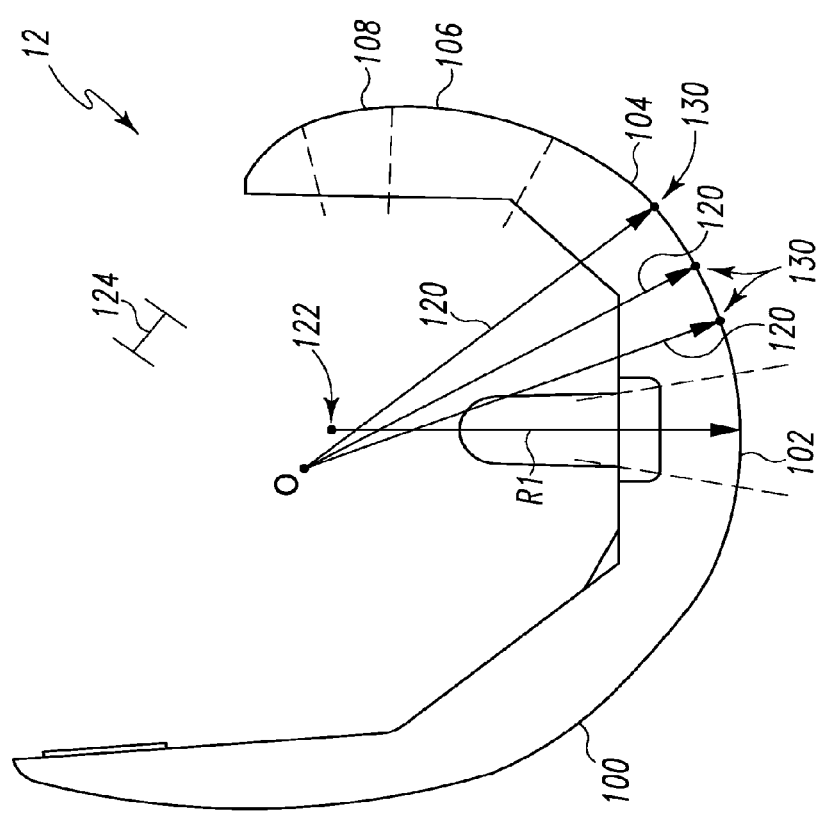
FIG. 11 is a cross-sectional view of one embodiment of a femoral component of the orthopaedic prosthesis of FIG. 1.

Referring now to FIG. 11, based on the above analysis of the equations (1) and (2), another way to reduce or delay the onset of paradoxical anterior translation of the femoral component 12 on the tibial bearing 14 is to gradually transition between the discrete radius of curvatures such that the change in the radius of curvature of the condyle surface 100 over a range of degrees of flexion is reduced. As such, in one embodiment, the early flexion curved surface section 104 is designed to provide a gradual transition from the first radius of curvature R1 to the second radius of curvature R2. To do so, the curved surface section 104 is defined by a plurality of rays 120, which originate from a common origin O. Each of the plurality of rays 120 defines a respective contact point 130 on the curved surface section 104. Although only three rays 120 are illustrated in FIG. 11 for clarity of the drawing, it should be appreciated that an infinite number of rays 120 may be used to define the curved surface section 104.

The location of each contact points 130, which collectively define the curved surface section 104, can be determined based on the length of each ray 120 at each degree of flexion.

In particular and unexpectedly, it has been determined that paradoxical anterior translation of the femoral component 12 on the tibial bearing 14 may be reduced or delayed by defining the curved surface section 104 according to the following polynomial equation:

$$r_\theta=(a+(b*\theta)+(c*\theta^2)+(d*\theta^3)), \quad (3)$$

wherein "$r_\theta$" is the length of a ray 120 (in metric units) defining a contact point 130 on the curved surface section 104 at "θ" degrees of flexion, "a" is a scalar value between 20 and 50, and "b" is a coefficient value selected such that:

$$-0.30 < b < 0.00,$$

$$0.00 < b < 0.30, \text{ or}$$

$$b=0 \quad (4)$$

If the selected coefficient "b" is in the range of $-0.30 < b < 0.00$, then coefficients "c" and "d" are selected such that:

$$0.00 < c < 0.012, \text{ and}$$

$$-0.00015 < d < 0.00. \quad (5)$$

Alternatively, if the selected coefficient "b" is in the range of $0.00 < b < 0.30$, then coefficients "c" and "d" are selected such that:

$$-0.010 < c < 0.00, \text{ and}$$

$$-0.00015 < d < 0.00. \quad (6)$$

Further, if the selected coefficient "b" is equal to 0, then coefficients "c" and "d" are selected such that:

$$-0.0020 < c < 0.00, \text{ or}$$

$$0.00 < c < 0.0025, \text{ and}$$

$$-0.00015 < d < 0.00. \quad (7)$$

It should be appreciated that ranges of values for the scalar "a" and coefficients "b", "c", and "d" are a subset of an infinite number of possible solutions for the polynomial equation (3). That is, the particular set of ranges provided above have been determined from an infinite number of possibilities to generate a family of curves (i.e., the curved surface section 104) that provide a gradual transitioning of the condyle surface 100 from the radius of curvature R1 to the radius of curvature R2 such that anterior translation of the femoral component 12 relative to the tibial bearing 14 is reduced or delayed. Additionally, it should be appreciated that the range of values for each coefficient "a", "b", "c", and "d" are provided above in regard to embodiments designed using the metric system of units. However, such range of coefficient values may be converted for use in embodiments using other systems of units such as the English system of units.

The overall shape of the curved surface section 104 is also affected by the placement of the common origin O of the plurality of rays 120. By limiting the distance 124 between the common origin O of the plurality of rays 120 and the origin 122 of the radius of curvature R1, which defines the early flexion curved surface section 102, paradoxical anterior sliding of the femoral component 12 on the tibial bearing 14 may be reduced or delayed. As such, in one embodiment, the location of the common origin O of the plurality of rays 120 is selected such that the distance 124 between the common origin O and the origin 120 of the radius of curvature R1 is less than about 10 millimeters.

It should be appreciated that the distance 124 between the common origin O and the origin 122 of the radius of curvature R1 and the particular coefficient values may be dependent upon the particular size of the femoral component 12 in some embodiments. For example, as illustrated in FIG. 12, a table 700 illustrates one particular embodiment of coefficient values for the above-defined polynomial equation (3) and values for the distance 124 defined between the common origin O and the origin 122 of the radius of curvature R1. As shown in table 700, the distance 124 between the common origin O and the origin 122 of the radius of curvature R1 and the value for the scalar "a" change across the femoral component sizes. However, in this particular embodiment, the values for the coefficients "b", "c", and "d" are constant across the femoral component sizes. It should be appreciated, however, that in other embodiments, the coefficient values "b", "c", and "d" may change across the femoral component sizes.

Figure 13:
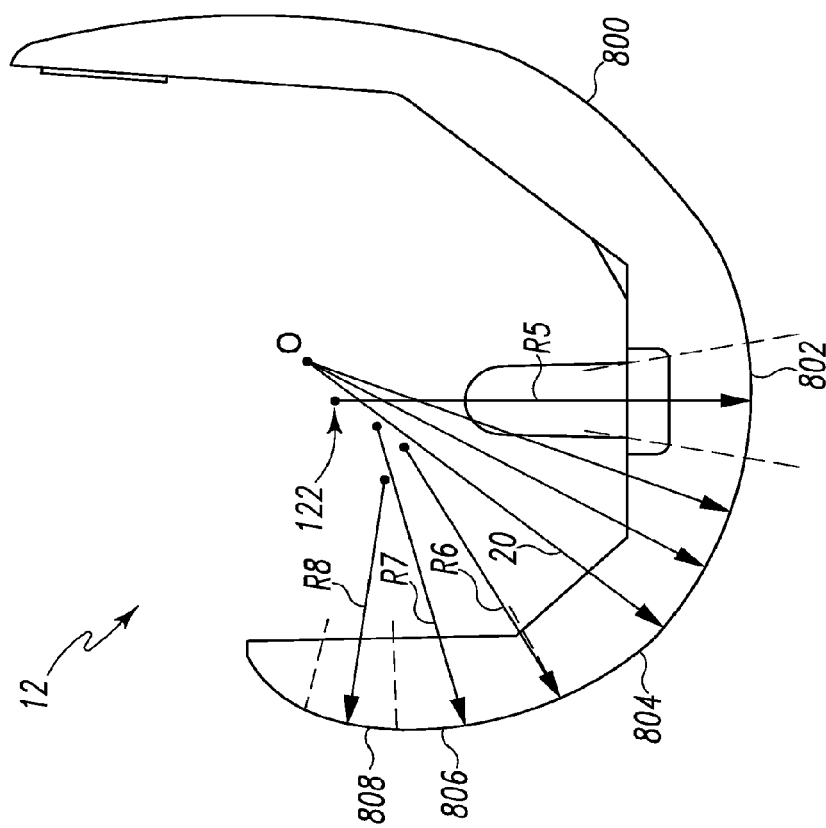
FIG. 13 is a cross-sectional view of another condyle of another embodiment of the femoral component of FIG. 1.

The overall shape and design of the condyle surface 100 of the femoral component 12 has been described above in regard to a single condyle 52, 54 of the femoral component 12. It should be appreciated that in some embodiments both condyles 52, 54 of the femoral component 12 may be symmetrical and have similar condyle surfaces 100. However, in other embodiments, the condyles 52, 54 of the femoral component 12 may be asymmetrical. For example, as illustrated in FIG. 13, the femoral component 12 may include a second condyle 52, 54 having a condyle surface 800, which is defined in part by a plurality of curved surface sections 802, 804, 806, 808. Similar to the curved surface sections 102, 104, 106, 108 of condyle surface 100, each of the curved surface sections 802, 804, 806, 808 are tangent to each adjacent curved surface section of the condyle surface 800. Additionally, the curved surface section 802 is defined by a radius of curvature R5, which is gradually transitioned to a radius of curvature R6 via the curved surface section 804. Similar to the curved surface section 104, the curved surface section 804 is defined by a plurality of rays 820, which originate from a common origin O1. Additionally, the curved surface section 806 is defined by a radius of curvature R7 and the curved surface section 808 is defined by a radius of curvature R8.

As such, in embodiments wherein the condyles 52, 54 are symmetrical, the curved surface sections 202, 802 extend between degrees of flexion that are substantially equal (i.e., each of the curved surface section 202, 802 may extend from a substantially equal earlier degree of flexion to a substantially equal later degree of flexion). Similarly, the curved surface sections 204, 804 extend between degrees of flexion that are substantially equal, the curved surface sections 206, 806 extend between degrees of flexion that are substantially equal, and the curved surface sections 208, 808 extend between degrees of flexion that are substantially equal. Additionally, the radius of curvature R5 is substantially equal to the radius of curvature R1, the radius of curvature R6 is substantially equal to the radius of curvature R2, the radius of curvature R7 is substantially equal to the radius of curvature R3, and the radius of curvature R8 is substantially equal to the radius of curvature R4. Further, the set of coefficient values "a","b", "c", and/or "d" of the equation (4) described above are substantially similar for both condyles.

However, in other embodiments, the condyles 52, 54 are asymmetrical. As such, the curved surface sections 202, 802 may extend between different degrees of flexion. Additionally, the curved surface sections 204, 804 may extend between different degrees of flexion, the curved surface sections 206, 806 may extend between different degrees of flexion, and the curved surface sections 207, 807 may extend between different degrees of flexion.

Additionally, in those embodiments wherein the condyles 52, 54 are asymmetrical, the radius of curvature R5 may be different from the radius of curvature R1, the radius of curvature R6 may be different from the radius of curvature R2, the radius of curvature R7 may be different from the radius of curvature R3, and/or the radius of curvature R8 may be different from the radius of curvature R4. Further, the set of coefficient values "a", b", "c", and/or "d" of the equation (3) described above may be different between the condyle surfaces 100 and 800.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic knee prosthesis comprising:
a femoral component having a condyle surface curved in the sagittal plane; and
a tibial bearing having a bearing surface configured to articulate with the condyle surface of the femoral component,
wherein the condyle surface (i) contacts the bearing surface at a first contact point on the condyle surface at a first degree of flexion, the first degree of flexion being less than about 30 degrees, (ii) contacts the bearing surface at a second contact point on the condyle surface at a second degree of flexion, the second degree of flexion being in the range of 45 degrees to 90 degrees, and (iii) contacts the bearing surface at a third contact point on the condyle surface at a third degree of flexion greater than the second degree of flexion,
wherein (i) the condyle surface in the sagittal plane has a first radius of curvature at the first contact point, (ii) the condyle surface in the sagittal plane has a second radius of curvature at the second contact point, (iii) the condyle surface in the sagittal plane has a third radius of curvature at the third contact point, (iv) the ratio of the first radius of curvature to the second radius of curvature is in the range of 1.10 to 1.45, and (v) the third radius of curvature being greater than the second radius of curvature by at least 0.5 millimeters,
wherein the condyle surface in the sagittal plane includes a first curved surface section defined between the first contact point and the second contact point, the first curved surface section having a non-constant radius of curvature.

2. The orthopaedic knee prosthesis of claim 1, wherein ratio of the first radius of curvature to the second radius of curvature is about 1.35.

3. The orthopaedic knee prosthesis of claim 1, wherein the first degree of flexion is in the range of 0 degrees to 10 degrees and the second degree of flexion is in the range of 60 degrees to 70 degrees.

4. The orthopaedic knee prosthesis of claim 3, wherein the first degree of flexion is about 5 degrees and the second degree of flexion is about 65 degrees.

5. The orthopaedic knee prosthesis of claim 1, wherein the ratio of the first radius of curvature to the third radius of curvature is in the range of 1.10 to 1.45.

6. The orthopaedic knee prosthesis of claim 5, wherein the ratio of the first radius of curvature to the third radius of curvature is about 1.28.

7. The orthopaedic knee prosthesis of claim 1, wherein the third degree of flexion is in the range of 80 degrees to 110 degrees.

8. The orthopaedic knee prosthesis of claim 7, wherein the third degree of flexion is about 90 degrees.

9. The orthopaedic knee prosthesis of claim 1, wherein:
(i) the condyle surface contacts the bearing surface at a fourth contact point on the condyle surface at a fourth degree of flexion, the fourth degree of flexion being greater than the third degree of flexion, and
(ii) the condyle surface in the sagittal plane has a fourth radius of curvature at the fourth contact point, the fourth radius of curvature being less than the third radius of curvature.

10. The orthopaedic knee prosthesis of claim 9, wherein the ratio of the first radius of curvature to the fourth radius of curvature is in the range of 1.10 to 1.45.

11. The orthopaedic knee prosthesis of claim 10, wherein the ratio of the first radius of curvature to the fourth radius of curvature is about 1.305.

12. The orthopaedic knee prosthesis of claim 9, wherein the fourth degree of flexion is in the range of 90 degrees to 120 degrees.

13. The orthopaedic knee prosthesis of claim 12, wherein the third degree of flexion is about 105 degrees.

14. The orthopaedic knee prosthesis of claim 9, wherein the ratio of the first radius of curvature to the second radius of curvature is about 1.35, the ratio of the first radius of curvature to the third radius of curvature is about 1.28, and the ratio of the first radius of curvature to the third radius of curvature is about 1.305.

15. The orthopaedic knee prosthesis of claim 9, wherein:
the condyle surface of the femoral component in the sagittal plane includes (i) a second curved surface section defined between the second contact point and the third contact point and (ii) a third curved surface section defined between the third contact point and the fourth contact point,
the second curved surface section having a substantially constant radius of curvature substantially equal to the third radius of curvature, and
the third curved surface section having a substantially constant radius of curvature substantially equal to the fourth radius of curvature.

16. The orthopaedic knee prosthesis of claim 1, wherein:
the condyle surface contacts the bearing surface at a plurality of contact points between the first contact point and the second contact point when the femoral component is moved from the first degree of flexion to the second degree of flexion, and
each contact point of the plurality of contact points is defined by a ray extending from a common origin to the respective contact point of the plurality of contact points, each ray having a length defined by the following polynomial equation:

$$r_\theta = (a + (b*\theta) + (c*\theta^2) + (d*\theta^3)),$$

wherein $r_\theta$ is the length of the ray defining a contact point at θ degrees of flexion, a is a coefficient value between 20 and 50, and b is a coefficient value in a range selected from the group consisting of: −0.30<b<0.00, 0.00<b<0.30, and b=0, wherein when b is in the range of −0.30<b<0.00, (i) c is a coefficient value between 0.00 and 0.012 and (ii) d is a coefficient value between −0.00015 and 0.00, wherein when b is in the range of 0<b<0.30, (i) c is a coefficient value between −0.010 and 0.00 and (ii) d is a coefficient value between −0.00015 and 0.00, and wherein when b is equal to 0, (i) c is a coefficient value in a range selected from the group consisting of: −0.0020<c<0.00 and 0.00<c<0.0025 and (ii) d is a coefficient value between −0.00015 and 0.00.

17. The orthopaedic knee prosthesis of claim 16, wherein:
the first radius of curvature has an origin, and
the distance between the origin of the first radius of curvature and the common origin of the rays is in the range of 0 and 10 millimeters.

18. The orthopaedic knee prosthesis of claim 1, wherein the femoral component is a posterior cruciate-retaining femoral component.

19. An orthopaedic knee prosthesis comprising:
a femoral component having a condyle surface curved in the sagittal plane; and
wherein the condyle surface (i) contacts a bearing surface of a tibial bearing at a first contact point on the condyle surface at a first degree of flexion, the first degree of flexion being less than about 30 degrees, (ii) contacts the bearing surface at a second contact point on the condyle surface at a second degree of flexion, the second degree of flexion being in the range of 45 degrees to 90 degrees, and (iii) contacts the bearing surface at a plurality of contact points between the first contact point and the second contact point when the femoral component is moved from the first degree of flexion to the second degree of flexion, wherein each contact point of the plurality of contact points is defined by a ray extending from a common origin to the respective contact point of the plurality of contact points, each ray having a length defined by the following polynomial equation:

$$i\; r_\theta = (a + (b*\theta) + (c*\theta^2) + (d*\theta^3))$$

wherein $r_\theta$ is the length of the ray defining a contact point at θ degrees of flexion, a is a coefficient value between 20 and 50, and b is a coefficient value in a range selected from the group consisting of: −0.30<b<0.00, 0.00<b<0.30, and b=0, wherein when b is in the range of −0.30<b<0.00, (i) c is a coefficient value between 0.00 and 0.012 and (ii) d is a coefficient value between −0.00015 and 0.00, wherein when b is in the range of 0<b<0.30, (i) c is a coefficient value between −0.010 and 0.00 and (ii) d is a coefficient value between −0.00015 and 0.00, and wherein when b is equal to 0, (i) c is a coefficient value in a range selected from the group consisting of: −0.0020<c<0.00 and 0.00<c<0.0025 and (ii) d is a coefficient value between −0.00015 and 0.00.

\* \* \* \* \*